(12) United States Patent
Yoneno et al.

(10) Patent No.: US 7,581,584 B2
(45) Date of Patent: Sep. 1, 2009

(54) AIR CONDITIONING SEAT DEVICE

(75) Inventors: Noriyuki Yoneno, Soraku-gun (JP);
Hiroshi Uno, Nara (JP); Fumitaka Kikutani, Soraku-gun (JP); Koichi Nakano, Sakai (JP); Shintaro Nozawa, Soraku-gun (JP); Satoshi Arima, Ikoma (JP); Mitsuru Yoneyama, Ikoma (JP); Yoshifumi Moriya, Nara (JP)

(73) Assignee: Panasonic Corporation, Osaka (JP)

( * ) Notice: Subject to any disclaimer, the term of this patent is extended or adjusted under 35 U.S.C. 154(b) by 827 days.

(21) Appl. No.: 10/507,759

(22) PCT Filed: Mar. 18, 2003

(86) PCT No.: PCT/JP03/03233

§ 371 (c)(1),
(2), (4) Date: Sep. 15, 2004

(87) PCT Pub. No.: WO03/077710

PCT Pub. Date: Sep. 25, 2003

(65) Prior Publication Data

US 2005/0188849 A1    Sep. 1, 2005

(30) Foreign Application Priority Data

| Mar. 19, 2002 | (JP) | ............................. 2002-075725 |
| Mar. 19, 2002 | (JP) | ............................. 2002-075747 |
| Apr. 9, 2002 | (JP) | ............................. 2002-106160 |
| Aug. 27, 2002 | (JP) | ............................. 2002-246525 |
| Aug. 27, 2002 | (JP) | ............................. 2002-246526 |

(51) Int. Cl.
*B60H 1/00* (2006.01)

(52) U.S. Cl. ...................................... 165/202; 165/204
(58) Field of Classification Search ......... 165/202–205, 165/214; 297/452.46
See application file for complete search history.

(56) References Cited

U.S. PATENT DOCUMENTS

| 4,926,618 | A | * | 5/1990 | Ratliff ............................ 95/10 |
| 5,230,466 | A | * | 7/1993 | Moriya et al. ............. 236/44 A |
| 5,450,594 | A | * | 9/1995 | Aden et al. .................. 709/225 |
| 5,524,439 | A | * | 6/1996 | Gallup et al. ................. 62/3.5 |
| 5,542,259 | A | * | 8/1996 | Worek et al. ................... 62/94 |
| 5,626,021 | A | * | 5/1997 | Karunasiri et al. ............ 62/3.5 |

(Continued)

FOREIGN PATENT DOCUMENTS

DE    197 37 636 A1    3/1999

(Continued)

OTHER PUBLICATIONS

International Search Report corresponding to application No. PCT/JP03/03233 dated Jun. 17, 2003.

*Primary Examiner*—Ljiljana (Lil) V Ciric
(74) *Attorney, Agent, or Firm*—RatnerPrestia

(57) ABSTRACT

An air conditioning seat device includes an air blower, and a dehumidifier for dehumidifying the air sent from the air blower owing to adsorption, and blows out the dehumidified air to holes provided on a skin of a seat through an air duct. In this makeup, the sweat on the body surface and in the clothes is rapidly vaporized, causing a large amount of vaporization heat loss. Accordingly, the human body feels coolness, and steaminess on the skin is suppressed owing to the sweat vaporization.

18 Claims, 22 Drawing Sheets

U.S. PATENT DOCUMENTS

| | | | | |
|---|---|---|---|---|
| 5,902,014 | A | * | 5/1999 | Dinkel et al. ............ 297/452.43 |
| 5,934,748 | A | * | 8/1999 | Faust et al. ............ 297/180.12 |
| 6,059,018 | A | * | 5/2000 | Yoshinori et al. ............. 165/42 |
| 6,062,641 | A | * | 5/2000 | Suzuki et al. ............ 297/180.1 |
| 6,064,037 | A | * | 5/2000 | Weiss et al. ................. 219/217 |
| 6,079,485 | A | * | 6/2000 | Esaki et al. ................... 165/43 |
| 6,092,375 | A | * | 7/2000 | Denniston ...................... 62/94 |
| 6,105,667 | A | * | 8/2000 | Yoshinori et al. ........... 165/202 |
| 2002/0096931 | A1 | * | 7/2002 | White et al. ........... 297/452.42 |

FOREIGN PATENT DOCUMENTS

| | | | |
|---|---|---|---|
| JP | 60-193412 | | 10/1985 |
| JP | 11-123925 | | 5/1999 |
| JP | 11-123959 | | 5/1999 |
| JP | 11123925 A | * | 5/1999 |
| JP | 11123931 A | * | 5/1999 |
| JP | 11123959 A | * | 5/1999 |
| JP | 2000-257960 | | 9/2000 |
| JP | 2002228189 A | * | 8/2002 |

* cited by examiner

FIG. 22
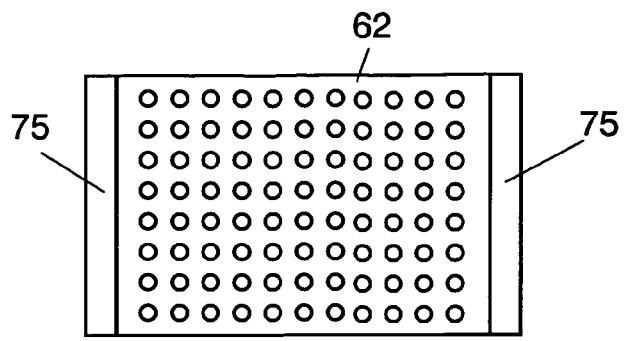
FIG. 23
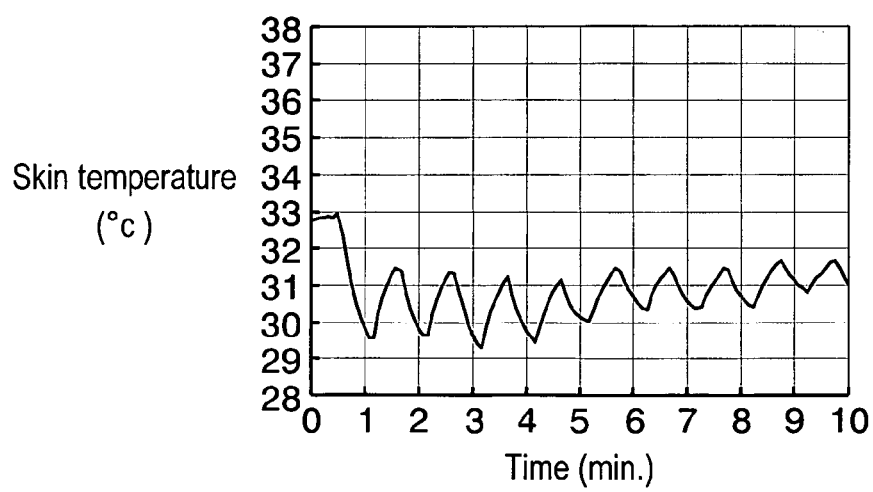
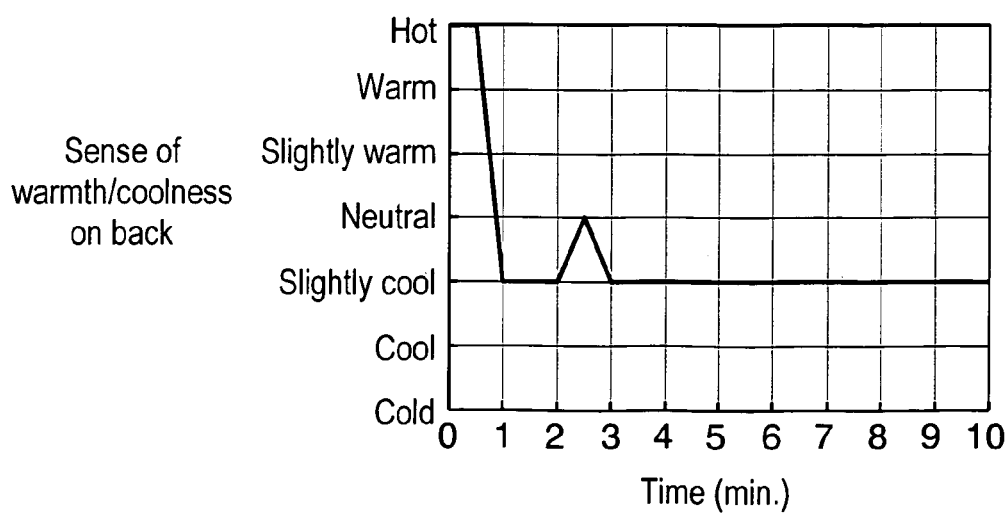

AIR CONDITIONING SEAT DEVICE

This application is a U.S. National phase application of PCT international Application PCT/JP03/03233.

TECHNICAL FIELD

The present invention relates to an air conditioning seat device, used for a chair in an automobile, an office, and the like, that provides a sense of comfortable seating even at a high environmental temperature and for a long-time seating.

BACKGROUND ART

A first conventional example of this type of air conditioning seat device is shown in FIG. 24. Such an air conditioning seat device has seat 3 for an automobile including backrest 1 and seating position 2, and Peltier module 4. Main heat exchanger 5 and waste-heat heat exchanger 6 are connected to Peltier module 4. Main heat exchanger 5 cools or warms airflow, and waste-heat heat exchanger 6 heat-exchanges waste heat with airflow. Airflow blowout holes (hereinafter referred to as "holes") 8 provided on skin cover 7 of seat 3 blow out airflow. Air duct 9 provided inside backrest 1 and seating part 2, communicating main heat exchanger 5 and holes 8, conveys airflow to be blown out through holes 8. Waste-heat air duct 10 conveys waste-heat airflow from waste-heat heat exchanger 6. Main fan 11 and auxiliary fan 12 convey airflow to main heat exchanger 5 and waste-heat heat exchanger 6, each connected to Peltier module 4, respectively. Temperature sensor 13 is mounted to Peltier module 4 at the side of main heat exchanger 5. Controller 14, in response to an output from temperature sensor 13, controls electric power application to Peltier module 4, and fans 11 and 12.

While a user drives the automobile, Peltier module 4, main fan 11, and auxiliary fan 12 are activated. In summer, airflow conveyed by main fan 11 is cooled by heat transfer from Peltier module 4, in main heat exchanger 5, is conveyed through air duct 9, and blows out as cool air through holes 8. Waste-heat airflow is warmed by heat transfer from Peltier module 4, in waste-heat heat exchanger 6, and blows out as waste heat through waste-heat air duct 10. Meanwhile, in winter, airflow conveyed by main fan 11 is warmed by heat transfer from Peltier module 4, in main heat exchanger 5, is conveyed through air duct 9, and blows out as warm air through holes 8. The waste-heat airflow is cooled by heat transfer from Peltier module 4, in waste-heat heat exchanger 6, and blows out as waste heat through waste-heat air duct 10. In this way, the back and buttocks of a vehicle occupant are cooled or warmed for air-conditioning a seat in the first conventional example, which is disclosed in Japanese Translation of PCT Publication No. H09-505497.

In addition, as a second conventional example, Japanese Patent Application Unexamined Publication No. S60-193412 discloses the following as shown in FIG. 25. This seat air-conditioning apparatus has a built-in air bag 23 in the main part of seat 21, that forcibly sucks outside air through skin cloth 22, a part of the main part of seat 21, which touches a human back. Further, the apparatus has built-in dehumidifier/dryer 26 in the headrest, which dehumidifies and dries outside air sucked by air bag 23, and exhausts it through air bag 23 to the human back. Dehumidifier/dryer 26 includes cooler/dehumidifier 24 and heater/dryer 25. Inlet air duct 27 and outlet air duct 28 allows dehumidifier/dryer 26 and air bag 23 to communicate. In the above-mentioned makeup, the outside air on the human back surface is sucked to air bag 23 through skin cloth 22. This outside air has a temperature of 32° C. and humidity of 80% (hereinafter, indicated as "80% RH"), for example. The outside air enters cooler/dehumidifier 24 through inlet air duct 27 to be cooled and dehumidified (condensing). The air after the process is in 15° C. and 100% RH, for example, which is further sent to heater/dryer 25 to be heated and dried. The air after the process is in 30° C. and 50% RH. The air processed in this way enters air bag 23 through outlet air duct 28, and blows out through skin cloth 22 toward the human back. This suppresses a sense of steaminess, preventing the body temperature from being lowered due to the cooled air.

In Japanese Patent Application Unexamined Publication No. H11-123959, a third conventional example is disclosed, where an absorbent material (a hygroscopic material) is used. As shown in FIGS. 26 through 28, backrest 29 has air duct 30 therein. Between backrest 29 and air duct 30, moisture-permeable layer 31 is arranged that permeates according to the gradient of a vapor partial pressure, and also that is air-impermeable. The vapor that permeates from backrest 29 flows into air duct 30 through moisture-permeable layer 31. Then, the air dried by air dryer unit 32 having a moisture-absorbing material flows into air duct 30. Accordingly, the vapor outside backrest 29 permeates moisture-permeable layer 31, and is absorbed in the dried air. FIG. 27 shows a makeup of air dryer unit 32, having reaction boxes 35 and 36. Reaction boxes 35 and 36 have air inlets 37 and 38, filled with an absorbent material such as zeolite or silica gel, and have integrated electric heaters 41 and 42, respectively. Air flap 34, electrically driven, switches the air flow between air outlet 40 connected to the inlet of air duct 30, and air outlet 39 open to the vehicle cabin. In the above-mentioned makeup, two reaction boxes 35 and 36 are alternately switched between the moisture-absorption process and the recycling process, for continuously running air dryer unit 32. While heater 41 is recycling reaction box 35 (recycling process), reaction box 36 performs a moisture-absorption process. In the moisture-absorption process, the adsorbent material performs a moisture-absorption action to dry the air flowing in the reaction box, and also heats the air by the heat of adsorption. When the adsorbent in reaction box 36 is saturated with moisture, air flap 34 is switched as shown by the broken line, and power is applied to heater 42 to recycle reaction box 36. At the same time, reaction box 35 dries the air flowing therein by a moisture-absorption action of the adsorbent material. Fan 43 may be allocated near air outlet 39 as shown in FIG. 28.

In summer, the temperature of a seat in a parked automobile rises to as high as approximately 60° C. by insolation. In such a situation, the air conditioning seat device of the first conventional example activates Peltier module 4 and main fan 11, cools airflow, and conveys it to holes 8. However, the temperature of skin cover 7 of seat 3 is approximately 60° C., and thus the temperature of skin cover 7 does not fall in a short time. Further, as the temperature of airflow decreases, its relative humidity increases. Because airflow blows out in this condition, a perspiring vehicle occupant feels steaminess, which is discomfort. Meanwhile, in winter, the apparatus activates Peltier module 4 and main fan 11, warms airflow, and blows it out through holes 8. The temperature-rise value at this time is determined by the warming heat quantity by Peltier module 4 and the airflow volume. The blowout temperature is determined by the ambient temperature with the temperature-rise value added, however, does not rise to a temperature at which the vehicle occupant feels warm if the ambient temperature is low.

In addition, the second conventional example requires a drain pipe for draining dew condensation water, because cooler/dehumidifier 24 dehumidifies. Therefore, a special modification is required for an automobile, or it is almost infeasible for a movable chair in an office.

In the third conventional example, moisture such as sweat from a human body is absorbed only at a portion contacting backrest 29, and the absorbed amount is small because moisture is absorbed through clothes and moisture-permeable layer 31.

SUMMARY OF THE INVENTION

An air conditioning seat device according to the present invention, including an air blower, and a dehumidifier for dehumidifying the air sent from the air blower owing to adsorption, blows out the dehumidified air to holes provided on a skin of a seat, through an air duct.

BRIEF DESCRIPTION OF THE DRAWINGS

FIG. 22 is a developed view of still another dehumidifier according to the eleventh exemplary embodiment of the present invention.

FIG. 23 illustrates an air-conditioning effect according to the embodiments of the present invention.

DETAILED DESCRIPTION OF PREFERRED EMBODIMENTS

Hereinafter, some embodiments of the present invention are described with reference to drawings. For similar components, the same mark is used and the detail description is omitted.

Exemplary Embodiment 1

Figure 1:
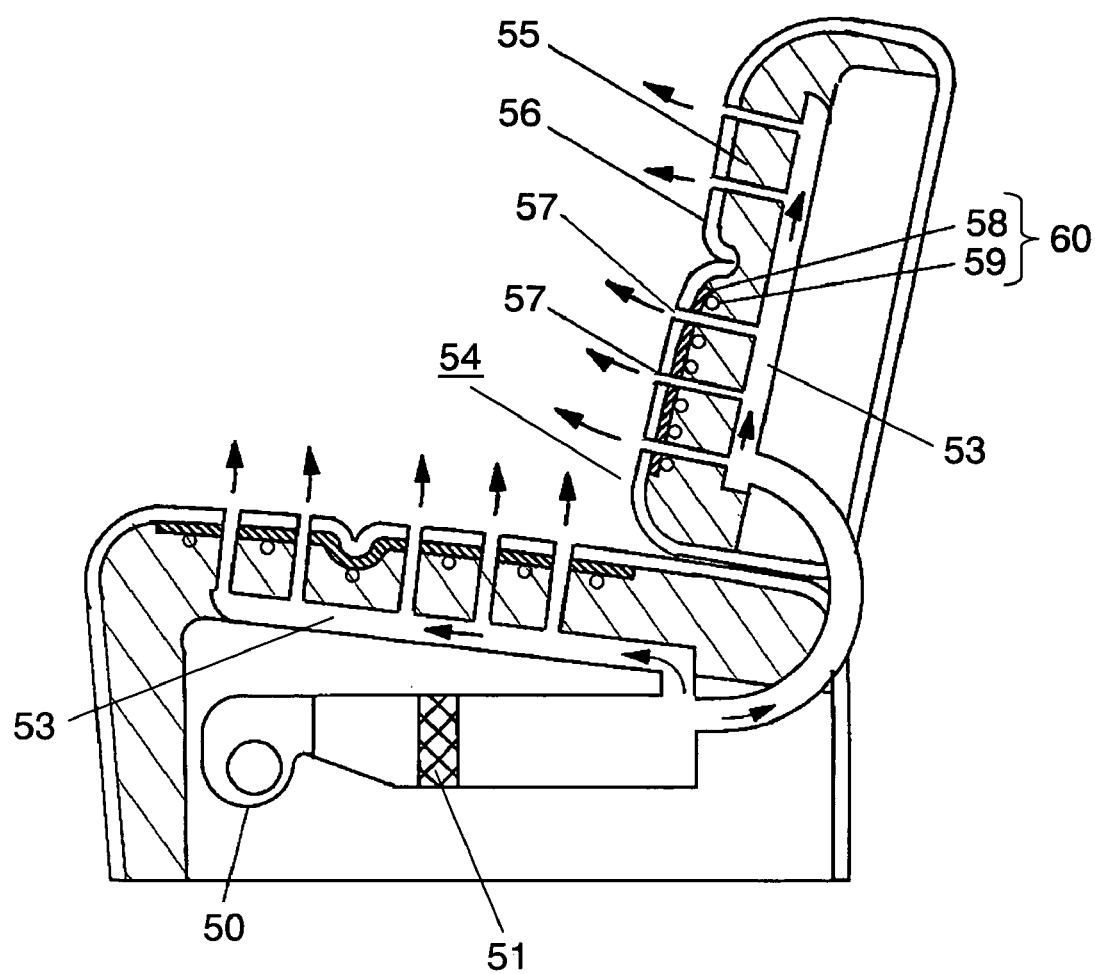
FIG. 1 is a sectional block diagram of an air conditioning seat device according to a first exemplary embodiment of the present invention.

FIG. 1 is a block,diagram of an air conditioning seat device according to a first exemplary embodiment of the present invention. Dehumidified air blower (hereinafter, "blower") 50 is a sirocco fan, for example. Dehumidifier 51, including an adsorbent such as zeolite, silica gel, titanium silicate, or activated alumina, dehumidifies the air sent by blower 50. Air duct 53 introduces dehumidified air to pad 55, made of a urethane foam resin, for example, of the main part of the seat (hereinafter, "seat") 54. Skin 56 covers pad 55, and is provided with blow-out holes (hereinafter, "holes") 57 through which the dehumidified air supplied from air duct 53 blows out.

Hereinafter, a description is made for how the air conditioning seat device as mentioned above acts and works.

While operating, dehumidifier 51 dehumidifies the air sent by blower 50. The dehumidified air passes from dehumidifier 51, through air duct 53, to pad 55, and then blows out through holes 57 of skin 56. A vehicle occupant is seated on seat 54, where the dehumidified air is blown on his/her back, buttocks, and lower legs. In this way, the dehumidified air is blown on a region where the surface of a human body touches. Consequently, sweat is dried with vaporization, vaporization heat is lost from the skin surfaces, and thus a vehicle occupant is comfortably seated with a sense of coolness, and without a sense of steaminess due to sweat, even at a high temperature of skin 56 due to insolation in summer. The air in a vehicle cabin is for example in 35° C. and 55% RH. The air sent with a flow rate of 0.2 m³/min. for example, reduces its humidity with vapor adsorption, and also generates heat owing to adsorption, resulting in 48° C. and 18% RH for example. The processed air is introduced to air duct 53, blows out through holes 57, and flows on the back side of a vehicle occupant. In this case, the occupant is heated owing to a heat transmission from dehumidified air, and a contact heat transmission from skin 56, however, a sense of coolness is brought to the human body, because the sweat on the body surface and clothes rapidly vaporizes, causing a large amount of vaporization heat loss. Also, vaporization of sweat prevents steaminess of skin. Still, because an air conditioner usually works while the vehicle is being driven, the air inside the cabin is approximately 25° C. and 40% RH. Accordingly, air can be sent by blower 50 to prevent steaminess even the adsorbent does not sufficiently work.

As described above, in this embodiment, the dehumidification operation is performed only by the power applied to blower 50, and thus the power consumption of the automobile's battery is reduced. Further, in a low humidity of 50% RH through 60% RH, as compared with a dehumidification by condensation, this embodiment has a higher performance in dehumidification, causes more vaporization heat loss on a skin surface, gives more coolness, prevents steaminess due to sweat, and allows a vehicle occupant to be seated more comfortably.

While the vehicle is not used in summer, skin 56 becomes hot with a temperature higher than 60° C. This heat transfers to the dehumidifier, and moisture absorbed by the adsorbent in dehumidifier 51 is desorbed, allowing the dehumidification capability to recover. Operating blower 50 intermittently can make desorption efficient.

The air conditioning seat device according to this embodiment further includes heater 60 between skin 56 and pad 55. Heater 60 has a makeup including porous seat 58 made of woven textile of a heat resistance resin such as cotton or nylon, or unwoven fabric of the same, and heater wire 59 fixed thereto that is made of an electrical resistance heating element such as a metal thin wire or carbon fiber. In a heating operation in winter, applying power to heater 60 to heat causes the heat to be conducted to skin 56, and skin 56 to be heated. Warmed skin 56 makes a seated occupant warm via conduction and radiation of the heat. The air blown out through air duct 53 during the above-mentioned dehumidification mode passes through seat 58 of heater 60, and blows out onto skin 56. This makeup keeps the temperature of skin 56 higher as compared with heating by warm air. Further, the speed of temperature rise is high, and thus improving comfort. In addition, heater 60 does not prevent airflow from passing through in the dehumidification mode. Better still, after reaching a steady state, a high-temperature and low-humidity air blown out through holes 57 dries sweat partially perspired due to heater 60, on the human body, to warm without steaminess.

Air duct 53 is desirably made of an unabsorbent material such as an urethane resin. This causes high-temperature, low-humidity air generated in the dehumidifier to be sent to a human body without absorbing moisture in the air duct. Therefore, the vaporization heat loss owing to vaporization of sweat on a human surface gives coolness to the human body, as well as suppressing steaminess.

In addition, air duct 53 is desirably branched at pad 55 as shown in FIG. 1. This causes the dehumidified air to be uniformly supplied widely over the back and buttocks of a vehicle occupant, increasing comfort.

Exemplary Embodiment 2

Figure 2:
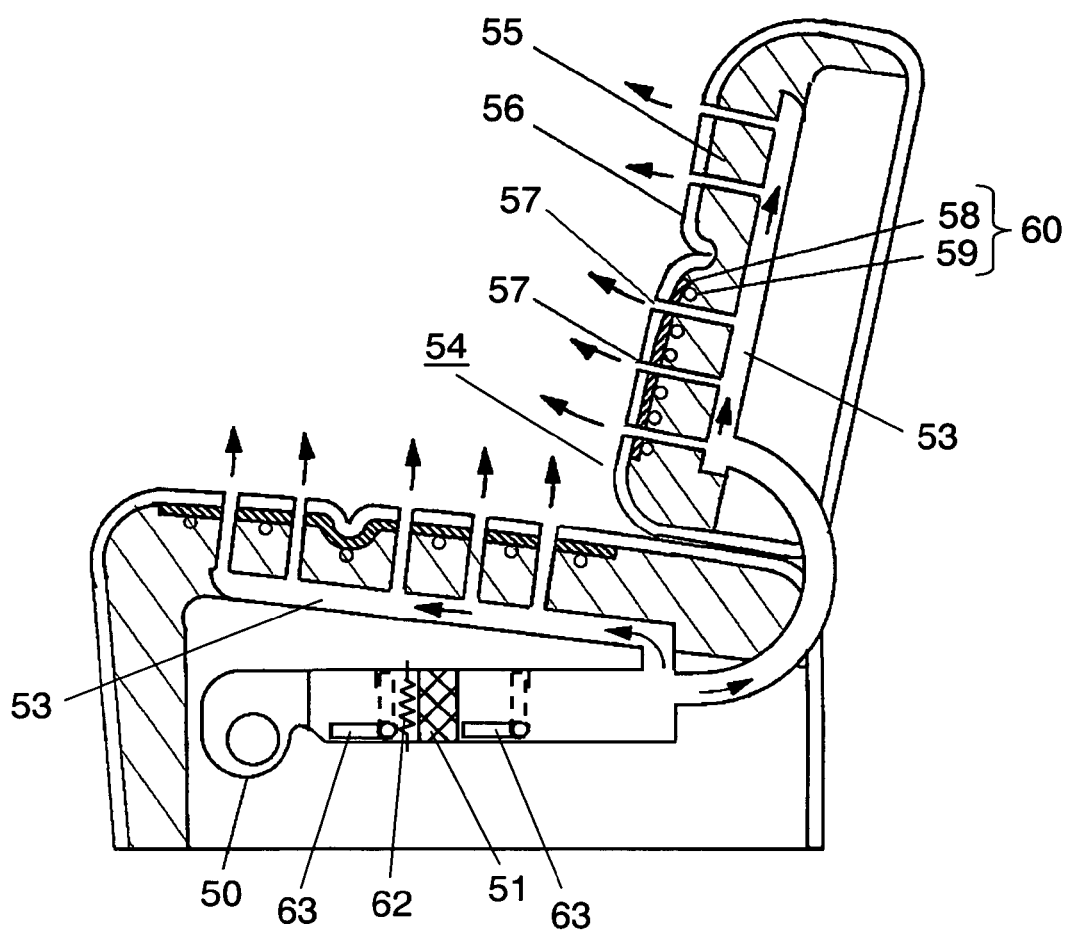
FIG. 2 is a sectional block diagram of an air conditioning seat device according to a second exemplary embodiment of the present invention.

FIG. 2 is a block diagram of an air conditioning seat device according to a second exemplary embodiment of the present invention. This embodiment differs from the first embodiment in having heater unit 62 for heating dehumidifier 51 owing to convection, radiation, or conduction, made of an electrical resistance heating element for example, and sealing part 63 for sealing dehumidifier 51.

Hereinafter, a description is made for how the air conditioning seat device in the above-mentioned makeup operates and works. Dehumidifier 51 incorporating an adsorbent needs to be dried in advance by emitting moisture before a dehumidification mode operation similar to the first embodiment. Alternatively, after a dehumidification mode operation, the moisture absorbed by dehumidifier 51 needs to be removed for reusing. For this, dehumidifier 51 is warmed by heater unit 62 to a desorb temperature at which the moisture is emitted. Then, the high-temperature, high-humidity air including the desorbed vapor passes through air duct 53 and discharged through holes 57 by blower 50. This recycle mode operation is performed while a vehicle occupant is not seated, in parking for example. This allows dehumidified air to be supplied through holes 57 without requiring the adsorbent included in dehumidifier 51 to be changed over a long period. Additionally, the air conditioning seat device can be operated with a maximum absorbability of dehumidifier 51, without requiring dew condensation water in dehumidifier 51 to be disposed.

After dehumidifier 51 finishes emitting moisture, heater unit 62 stops, and dehumidifier 51 is sealed by sealing part 63 as shown by the broken lines in the figure, and then enters a stand-by state. When a vehicle occupant gets aboard, sealing part 63 opens as shown by the solid lines in the figure, blower 50 sends the air in the cabin into dehumidifier 51 in a dry state. Such a makeup prevents dehumidifier 51 from adsorbing moisture in the atmospheric air, and the dehumidification capacity from being reduced in a stand-by state such as in parking. This is also effective for the makeup in the first embodiment, which does not include heater unit 62.

Heater unit 62 is desirably made of an expand-metal which is a lacinia-processed and expanded metal thin plate such as a stainless steel; a wire mesh which is a netted stainless-steel metal wire; or a porous member such as a punched stainless-steel thin plate. In the above-mentioned makeup, specifications of notch for lacinia of an expand-metal, elemental wire thickness and interval of weave pattern of a wire mesh, or punching specifications for hole diameter and pitch of punching metal can be easily changed. These changes allow the resistance value of the metallic body to be adjusted with ease and high accuracy, and thus a desired heating element can be easily obtained. Further, such a heater unit 62, a porous member, reduces the pressure loss of air blasting. In addition, heater unit 62, which is planar, can uniformly heat a large area, and thus dehumidifier 51 is uniformly heated, efficiently recycling the adsorbent.

If seat 58 of heater 60 is made of a woven textile of moisture-absorbing cotton fiber, or a moisture-absorbing member such as unwoven fabric, moisture in vapor always existing in the cabin is absorbed by diffusion while the seat is unoccupied such as in parking. In the dehumidification mode, when dehumidified air passes through air duct 53, seat 58, and then holes 57, the vapor accumulated in seat 58 is vaporized. At this moment, vaporization latent heat is removed so as to cool seat 58, and also the human body through skin 56. According to the above-mentioned makeup, seat 58 and skin 56 are cooled with low-humidity air, and thus coolness can be felt rapidly.

Exemplary Embodiment 3

Figure 3:
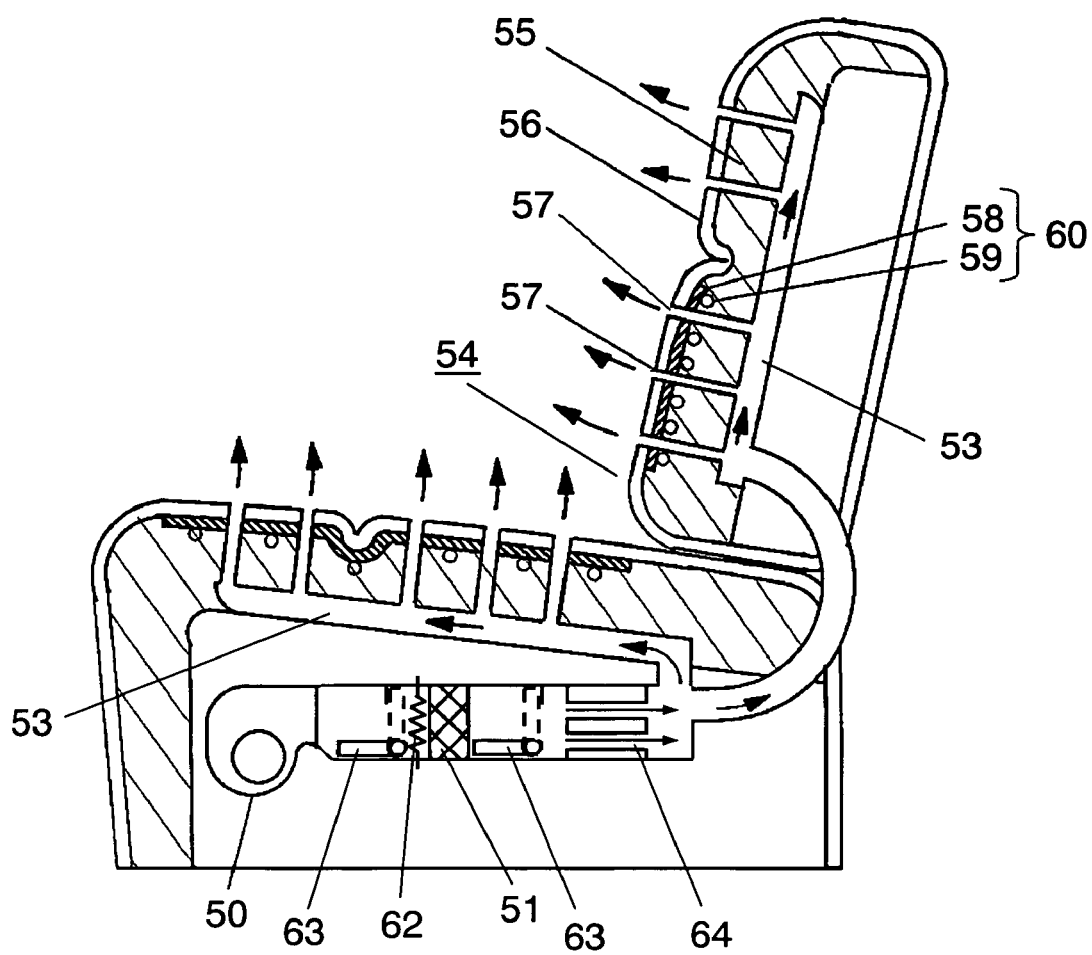
FIG. 3 is a sectional block diagram an air conditioning seat device according to a third exemplary embodiment of the present invention.

FIG. 3 is a block diagram of an air conditioning seat device according to a third exemplary embodiment of the present invention. This embodiment differs from the second embodiment in providing cooling heat exchanger 64 for cooling air having passed through dehumidifier 51.

Although the type of heat exchanger 64 is not limited, generally a plate-fin heat exchanger finned on partition walls heat-exchanges and cools the dehumidified air heated by the air inside the cabin. Also, the dehumidified air may be heat-exchanged with the seat bone and cooled. Still, a fan (Refer to FIG. 12.) for cooling heat exchanger 64 may be provided. The blow volume may be changed by controlling the blow volume according to the amount of heat generated. Further, heat exchanger 64 may be cooled by the blowout air from an air-conditioning device (not illustrated) for the cabin, for example. In addition, heat may be transferred to an automobile body for example, which has a higher heat capacity, from heat exchanger 64, by providing a heat conduction material that has a relation of heat transfer with heat exchanger 64. Alternatively, a heat storage material having a higher heat capacity than heat exchanger 64 may be arranged so that it has a relation of heat transfer with heat exchanger 64. Heat exchanger 64 may be cooled by a Peltier element. Heat exchanger 64 may be cooled by providing a pipe through which a coolant passes, and a device for cooling the coolant. Still, cooling air duct 53 in itself by blowing air, heat transfer, and the like is also effective in the same way as heat exchanger 64.

Hereinafter, a description is made for how the air conditioning seat device in the above-mentioned makeup operates and works. As described above, the moisture of the air in the cabin sent to dehumidifier 51 by blower 50 is absorbed in dehumidifier 51, and the humidity of the air is reduced. Simultaneously, the air is heated by the adsorption heat and enters a state of approximately 48° C. and 18% RH. This high-temperature, low-humidity air is introduced to heat exchanger 64, cooled by the cabin air, and becomes a low-humidity air with 37° C. and 33% RH, for example. Then, it is introduced to air duct 53, blows out through holes 57 of skin 56, and flows on the side of the human back. In this case, the human body has a small heat transmission from the dehumidified air, and vaporization heat loss owing to vaporization of the sweat on the body surface gives coolness to the human body.

As described above, this embodiment provides dry air without the temperature fluctuating. Therefore, even for a high setting temperature of an automobile air conditioner, this embodiment provides stronger coolness, prevents steaminess due to, sweat, and gives a sense of more comfortable seating to a vehicle occupant.

Exemplary Embodiment 4

Figure 4:
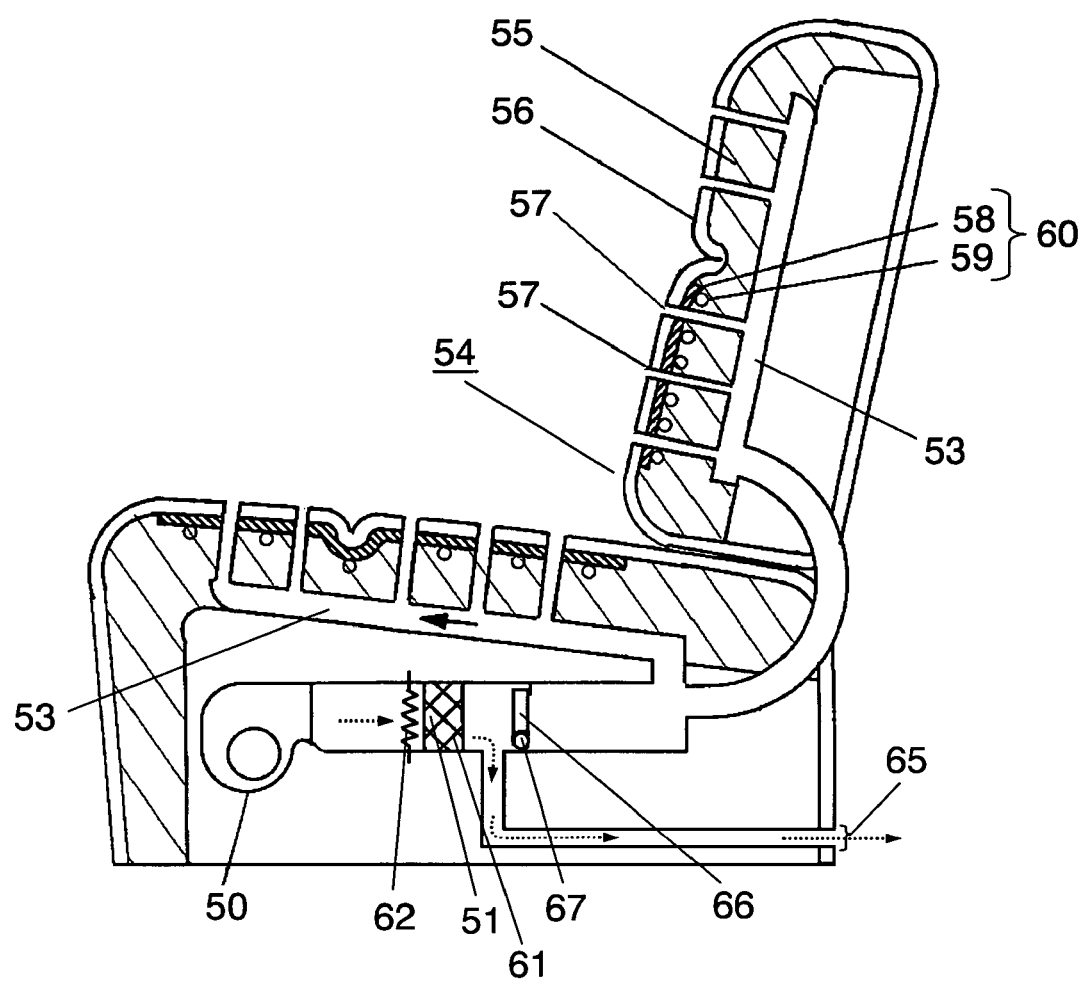
FIG. 4 is a sectional block diagram for illustrating the recycle mode in an air conditioning seat device according to a fourth exemplary embodiment of the present invention.
Figure 5:
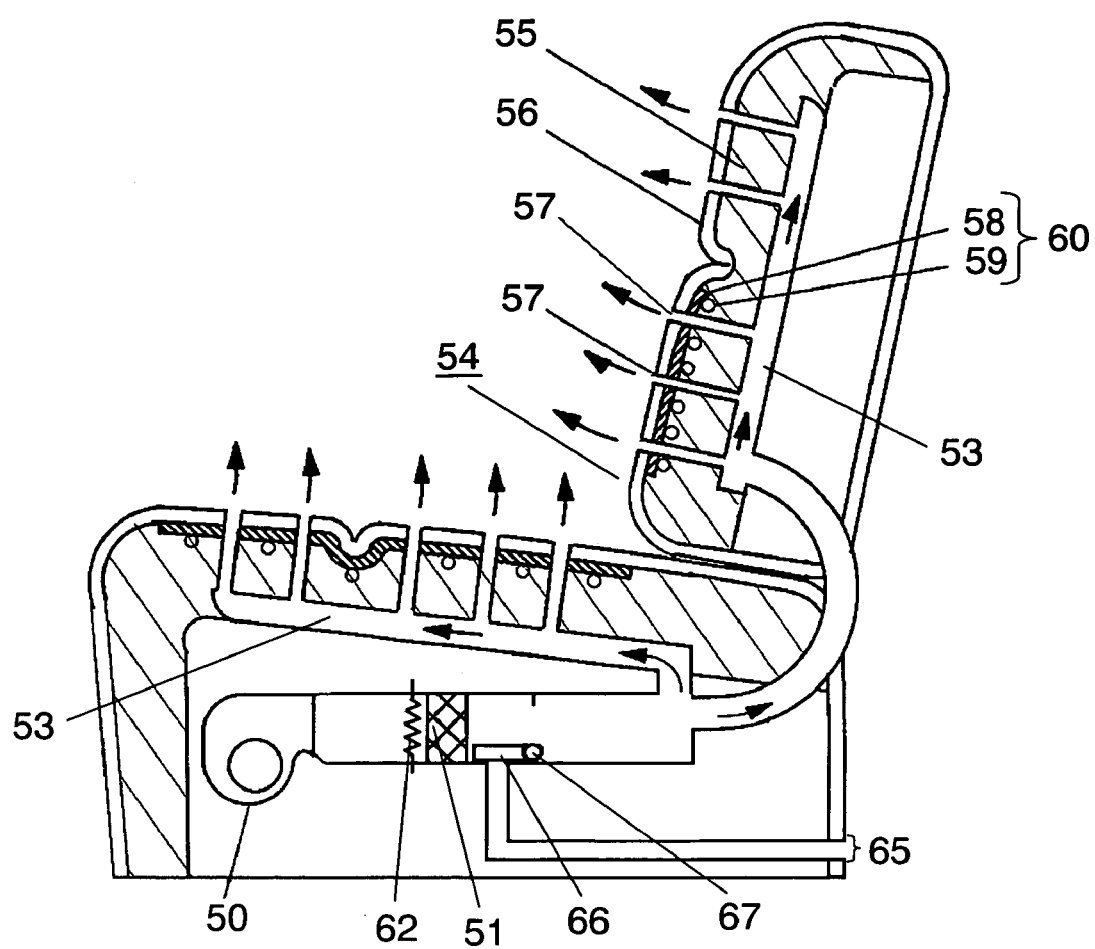
FIG. 5 is a sectional block diagram for illustrating the dehumidification mode in the air conditioning seat device according to the fourth exemplary embodiment of the present invention.
Figure 6:
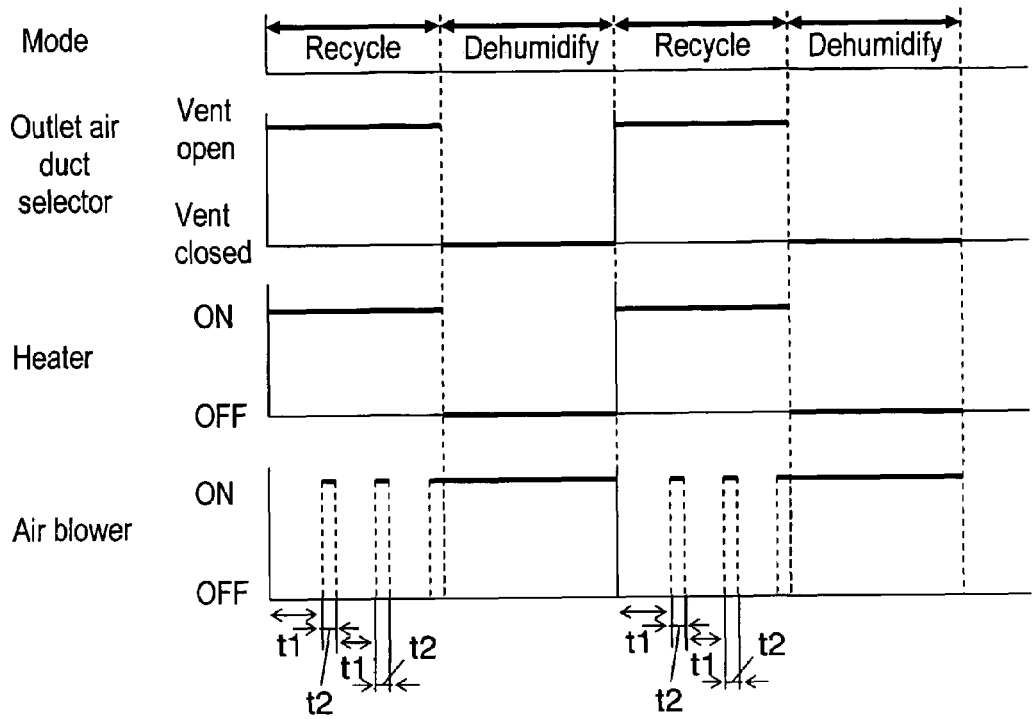
FIG. 6 is a time chart for the actions of each mode according to the fourth exemplary embodiment of the present invention.
Figure 7:
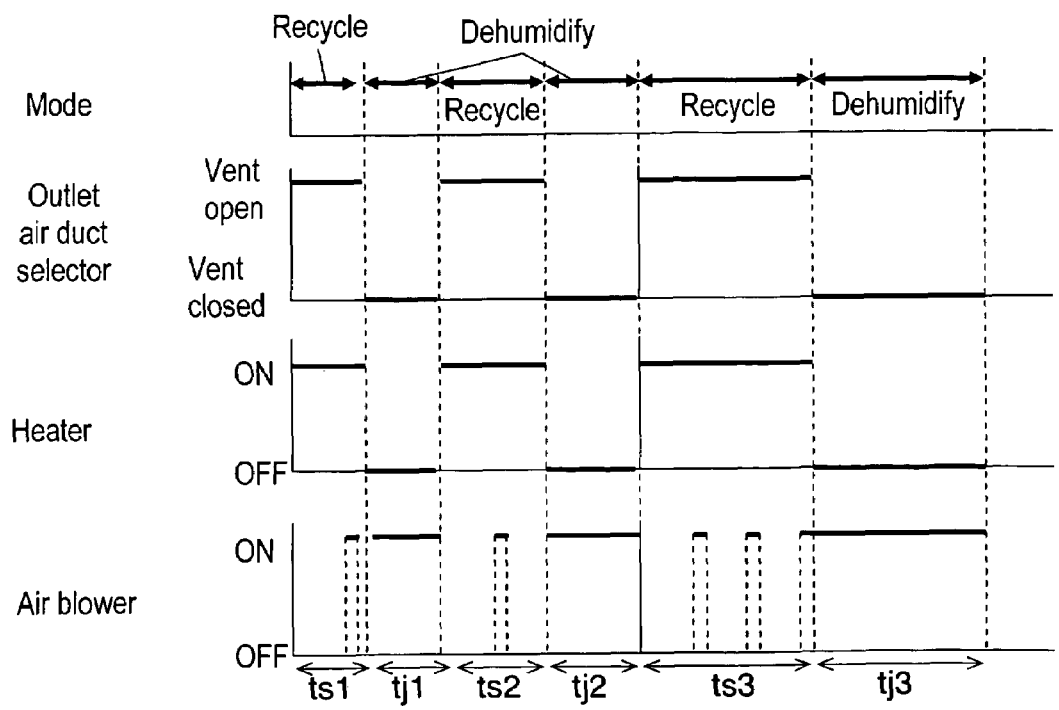
FIG. 7 is a time chart for the actions of each mode in another mode set, according to the fourth exemplary embodiment of the present invention.

FIG. 4 is a block diagram for illustrating the recycle mode in an air conditioning seat device according to a fourth exemplary embodiment of the present invention. FIG. 5 is a block diagram for illustrating the dehumidification mode. FIG. 6 is a time chart for the actions of each mode. FIG. 7 is a time chart for the actions of each mode in another mode set.

This embodiment differs from the first embodiment in having vent 65 communicating from dehumidifier 51 to the outside of the main body of the seat, and an outlet air duct selector (hereinafter, "selector") 66. Selector 66 opens a duct to vent 65 and closes air duct 53 in the recycle mode shown in FIG. 4. Meanwhile, in the dehumidification mode shown in FIG. 5, selector 66 closes the duct to vent 65, and opens air duct 53. Selector 66 is a damper for example, driven by such as stepping motor 67.

In the above-mentioned makeup, as shown in FIG. 6, the recycle mode operation is first performed. In other words, as in FIG. 4, dehumidifier 51 regains its dehumidification capability. Selector 66 switches to the position for opening the duct to vent 65, heater unit 62 is activated, and stops blower 50 at first for "t1" and then activates for "t2" with a flow rate of 0.2 m$^3$/min. for example. In FIG. 6, this operation is cycled with t1=20 seconds and t2=1 second. In the case that dehumidifier 51 has an adsorbent of silica gel, vapor starts desorbing off the adsorbent when the adsorbent is heated to 120° C. Then, blower 50 emits the generated vapor from vent 65 to inside the cabin. In this case, the heat generated in heater unit 62 transmits to the surface of adsorbent 61. At this time, when the surface of adsorbent 61 is in a low temperature, it isn't desirable to activate blower 50. To do so, the surface temperature of adsorbent 61 quickly rises and the vapor quickly desorbs off adsorbent 61. Further, sending air intermittently causes a higher surface temperature of the adsorbent than sending a low air-volume (for example, a flow rate of 0.02 m$^3$/min.) continuously. Therefore, the volume of heat transfer to the inside of adsorbent 61 becomes large according to Fourier's law, and the recycle time is reduced. In addition, adjusting the blow volume is unnecessary, and thus the makeup of the apparatus can be simplified.

After the recycle mode is completed, as shown in FIG. 6, the dehumidification mode operation is performed. Although the dehumidification mode is shown in FIG. 5, its description is omitted, because it is the same as the second embodiment except for switching selector 66.

As described above, the recycle mode operation is first performed, and then the dehumidification mode operation is performed in this embodiment. In the second embodiment, sealing part 63 seals dehumidifier 51. While in this embodiment, a sealing part is not provided. Therefore, after a long time since the previous operation, adsorbent 61 absorbs moisture with diffusion, decreasing the dehumidification capacity. Even in such a case, this type of operation allows absorbability of adsorbent 61 to be regained, and moisture-absorption capacity providing a human body with coolness when the dehumidification mode operation is performed for a long time, to be ensured.

In this embodiment, selector 66 and vent 65 are provided, which prevents high-temperature, high-humidity air from blowing out through holes 57, even if the recycle mode operation is performed while a vehicle occupant is seated. This reduces the load of the automobile battery due to activating heater unit 62 and blower 50 while the engine is at a stop for parking, for example.

The heater unit operating time in the initial recycle mode, "ts1", may be shorter than "ts2" and "ts3", the heater unit operating times in the next recycle mode and after. And the operating time in the initial dehumidification mode, "tj1", may be shorter than "tj2" and "tj3", the operating times in the next dehumidification mode and after. In FIG. 7, these values hold ts1<ts2<ts3, and tj1<tj2<tj3. Short ts1 allows the dehumidification operation to start early. Then, the time intervals between recycle modes and dehumidification modes are gradually extended to start a steady operation. This ensures an immediate effect and reduces discomfort due to changing to a steady state. In midsummer, the temperature in a cabin is high, so a request for rapid coolness is satisfied.

Exemplary Embodiment 5

Figure 8:
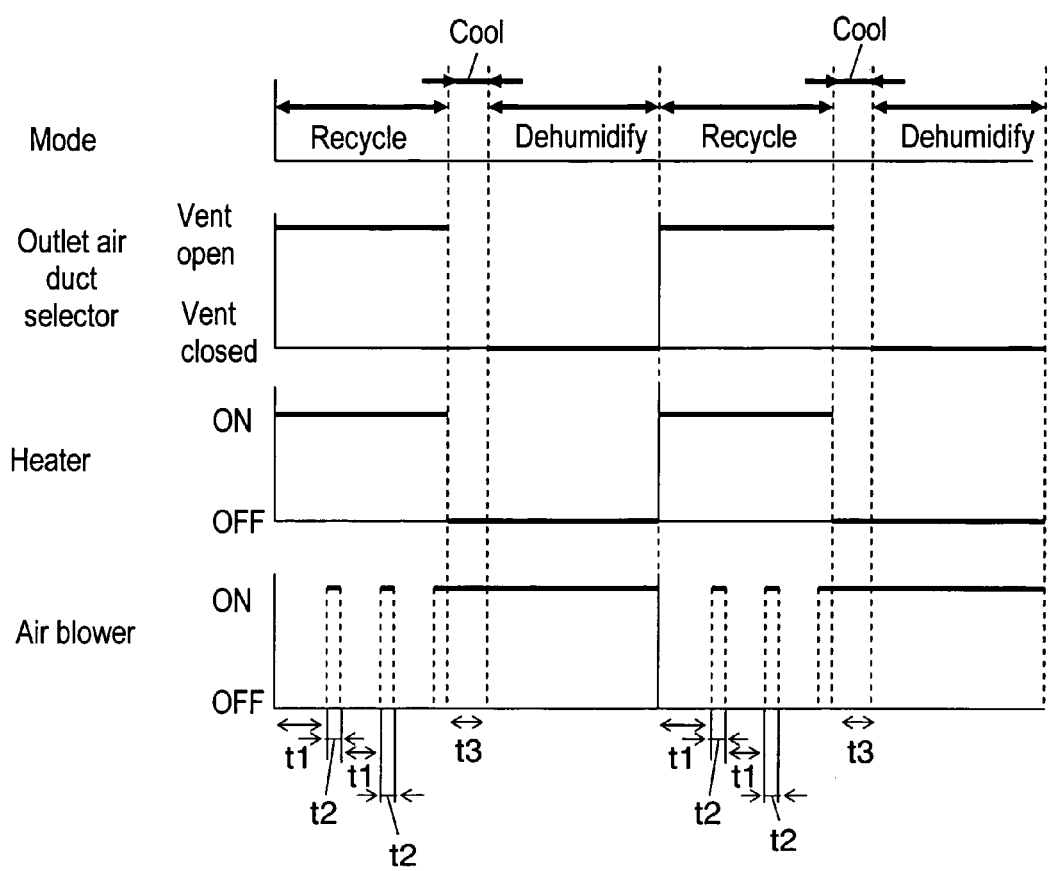
FIG. 8 is a time chart for the actions of each mode according to a fifth exemplary embodiment of the present invention.

FIG. 8 is a time chart for the actions of each mode according to a fifth exemplary embodiment. The basic makeup for an air conditioning seat device according to this embodiment is the same as in FIG. 4 and FIG. 5 in the fourth embodiment.

As shown in FIG. 8, a cooling mode operation is performed after the recycle mode for regaining dehumidification capability of dehumidifier 51, until entering the dehumidification mode. In the cooling mode operation, heater unit 62 stops and blower 50 is activated to decrease the temperature of adsorbent 61. After the cooling mode operation, selector 66 closes vent 65 and blower 50 is activated to perform the dehumidification mode operation. The above-mentioned makeup allows adsorbent 61 to be cooled in the cooling mode, although adsorbent 61 is in a high temperature after the recycle operation. Consequently, adsorbent 61 becomes vapor-adsorptive. Further, when the dehumidification mode operation is started, the air sent to dehumidifier 51 by blower 50 absorbs very little sensible heat of dehumidifier 51. Therefore, air with temperature higher than necessary does not blow out through holes 57, and thus it does not give discomfort to a vehicle occupant. In other words, the initial hot air immediately after changing to the dehumidification mode can be suppressed, which boosts coolness.

Exemplary Embodiment 6

Figure 9:
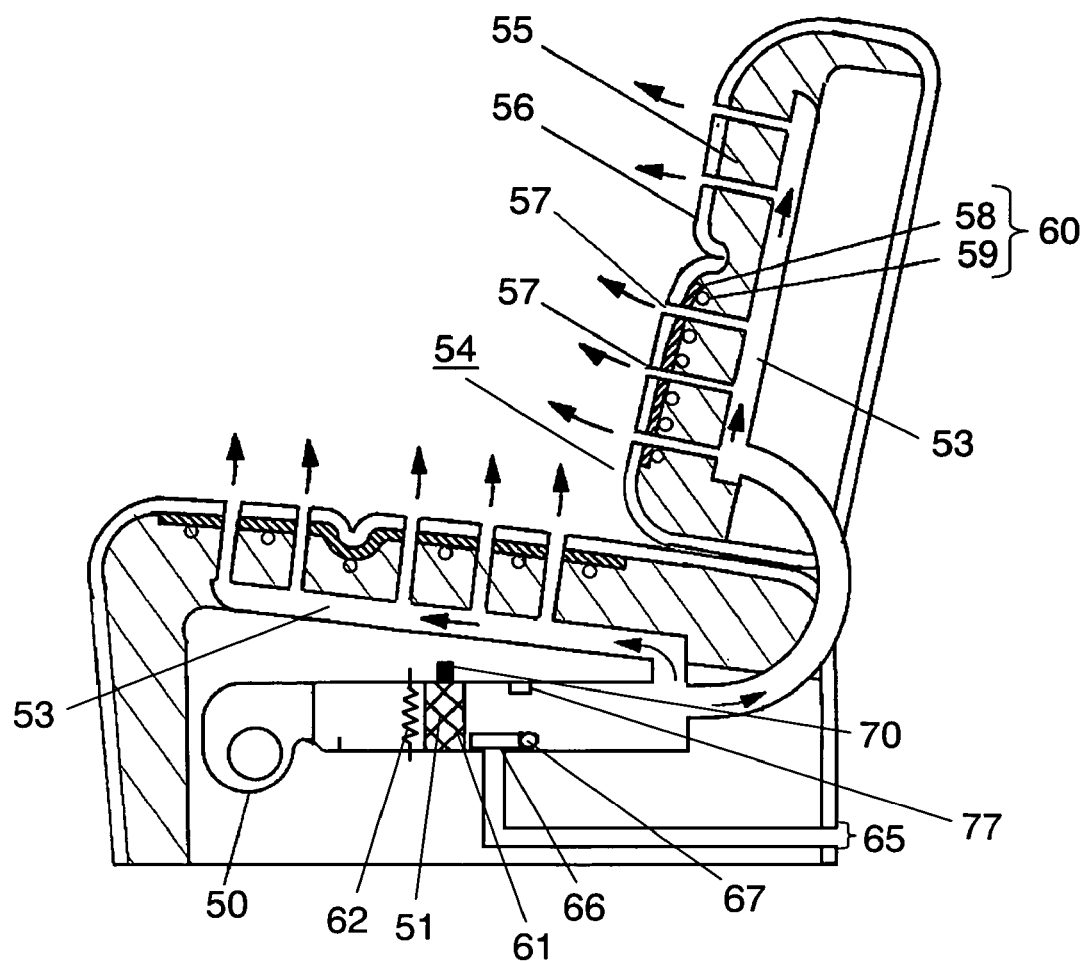
FIG. 9 is a sectional block diagram for illustrating the dehumidification mode in an air conditioning seat device according to a sixth exemplary embodiment of the present invention.
Figure 10:
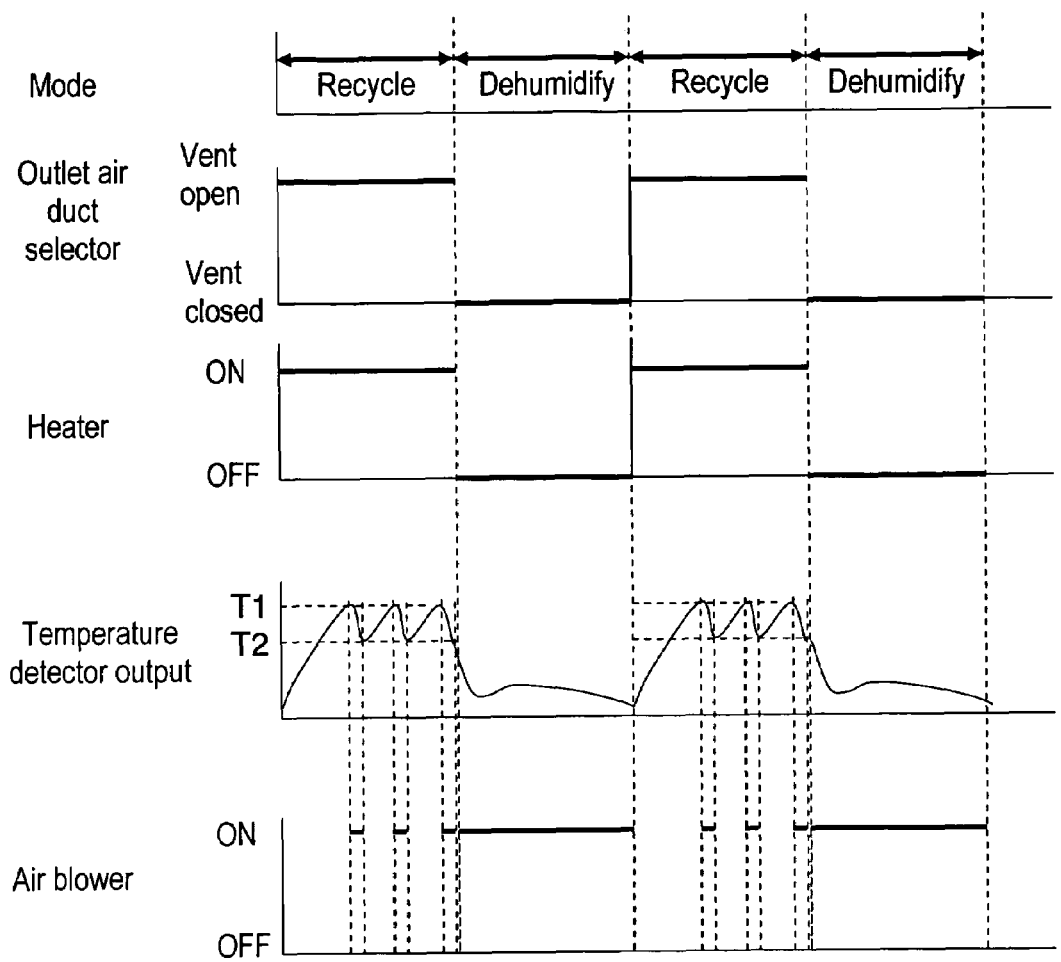
FIG. 10 is a time chart for the actions of each mode according to the sixth exemplary embodiment of the present invention.

FIG. 9 is a block diagram for illustrating the dehumidification mode in an air conditioning seat device according to a sixth exemplary embodiment of the present invention. FIG. 10 is a time chart for the actions of each mode. In this embodiment, in addition to the makeup in embodiment 4, temperature detector 70 for detecting the temperature of dehumidifier 51 is provided to control the actions of blower 50, heater unit 62, and selector 66. As shown in FIG. 10, selector 66 opens the duct to vent 65 and heater unit 62 is activated in the recycle mode. When the temperature measured by temperature detector 70 is the set value "T1" or higher, blower 50 is activated, and the temperature falls to "T2" or lower, blower 50 stops. In other words, when the adsorbent is heated to "T1" and vapor starts to desorb off the adsorbent, blower 50 is activated. By doing this, blower 50 is not operated until adsorbent 61 generates vapor, independently of outside-air temperature, and thus the temperature of adsorbent 61 rises quickly, enabling adsorbent 61 to be recycled rapidly and efficiently. In the case that adsorbent 61 is silica gel, it is desirable that "T1" and "T2" be set as 120° C. and 90° C., respectively.

In the case that adsorbent 61 is silica gel, the hydroxyl group of silica gel is destroyed at a temperature higher than 180° C., decreasing the adsorption capability. Therefore, when the output from temperature detector 70 is going to exceed 180° C., it is desirable to continuously operate blower 50, or to stop activating heater unit 62. In this way, deterioration of adsorbent 61 can be suppressed.

Figure 11:
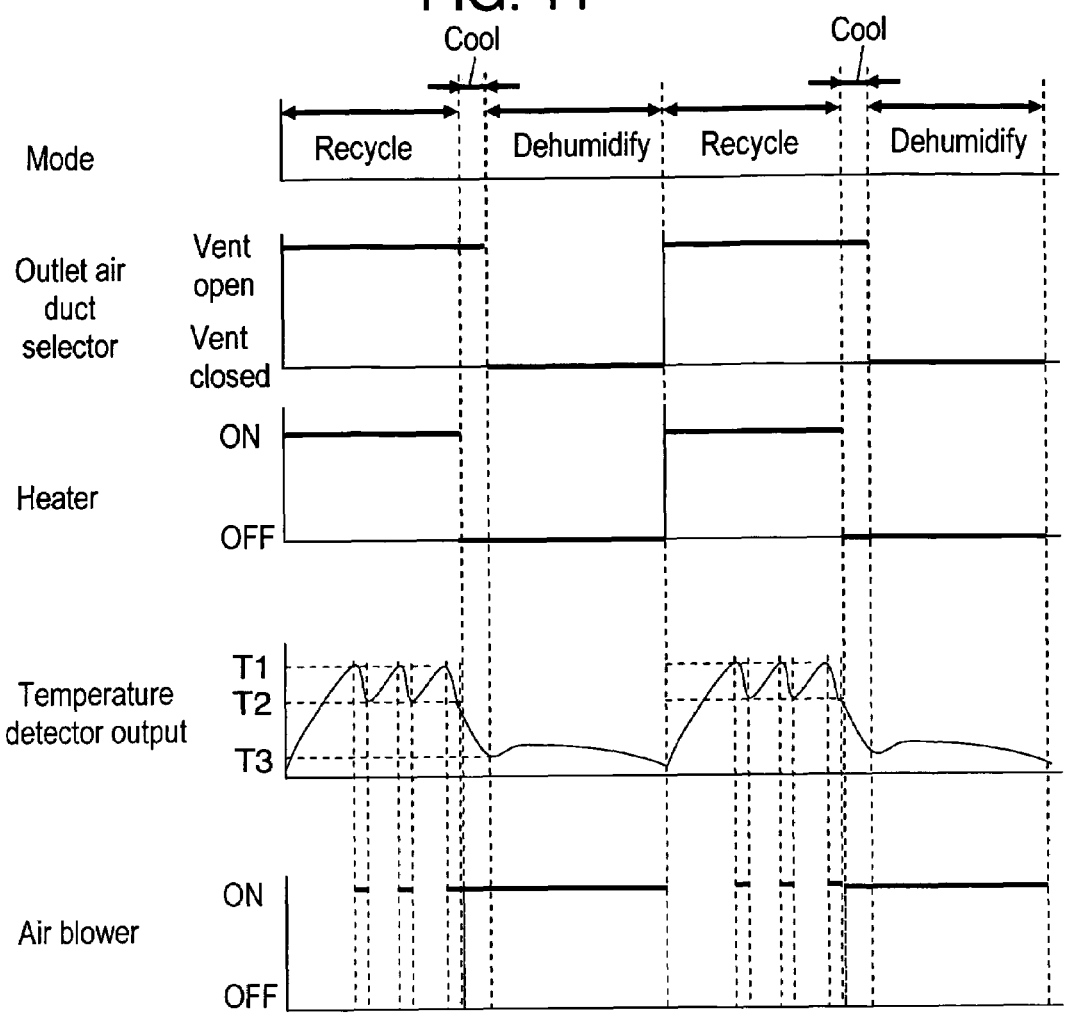
FIG. 11 is a time chart for the actions of each mode in another mode set according to the sixth exemplary embodiment of the present invention.

In addition, as shown by a time chart in FIG. 11, after dehumidifier 51 is recycled in the recycle mode, the cooling mode operation is performed, in which heater unit 62 stops and blower 50 is activated until dehumidifier 51 reaches set temperature "T3". With such a mode set, the cooling-mode operating time can be minimized, and the dehumidification operating time, during which coolness can be given to a human body, can be extended, independently of the outside-air temperature and the elapsed time after the operation has started.

In addition, humidity detector (hereinafter "detector") 77 for detecting the humidity of the air passed through dehumidifier 51 is provided in this embodiment. Detector 77 monitors the humidity of the processed air in the dehumidification mode. When the humidity of the processed air exceeds the predetermined one, the mode is controlled to enter the recycle mode. Such a mode set ensures performing dehumidification as compared with changing the mode at a fixed time interval. When starting the recycle mode operation, blower 50 once stops, selector 66 opens the duct to vent 65, and heater unit 62 is activated. When the value measured by detector 77 comes to a set value or higher, blower 50 is activated. This makes the temperature of dehumidifier 51 rise quickly.

Exemplary Embodiment 7

Figure 12:
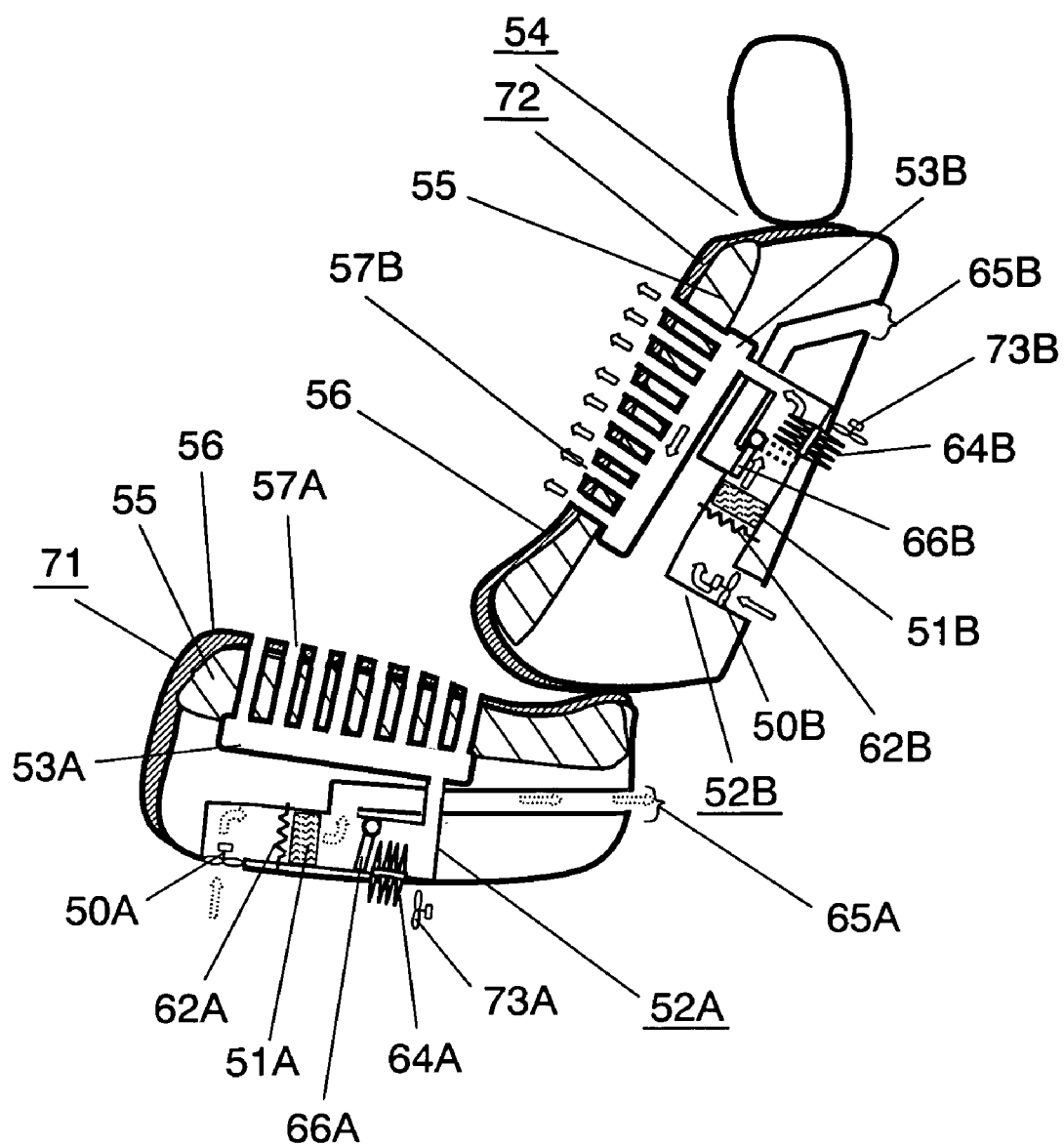
FIG. 12 is a sectional block diagram of an air conditioning seat device according to a seventh exemplary embodiment of the present invention.
Figure 13:
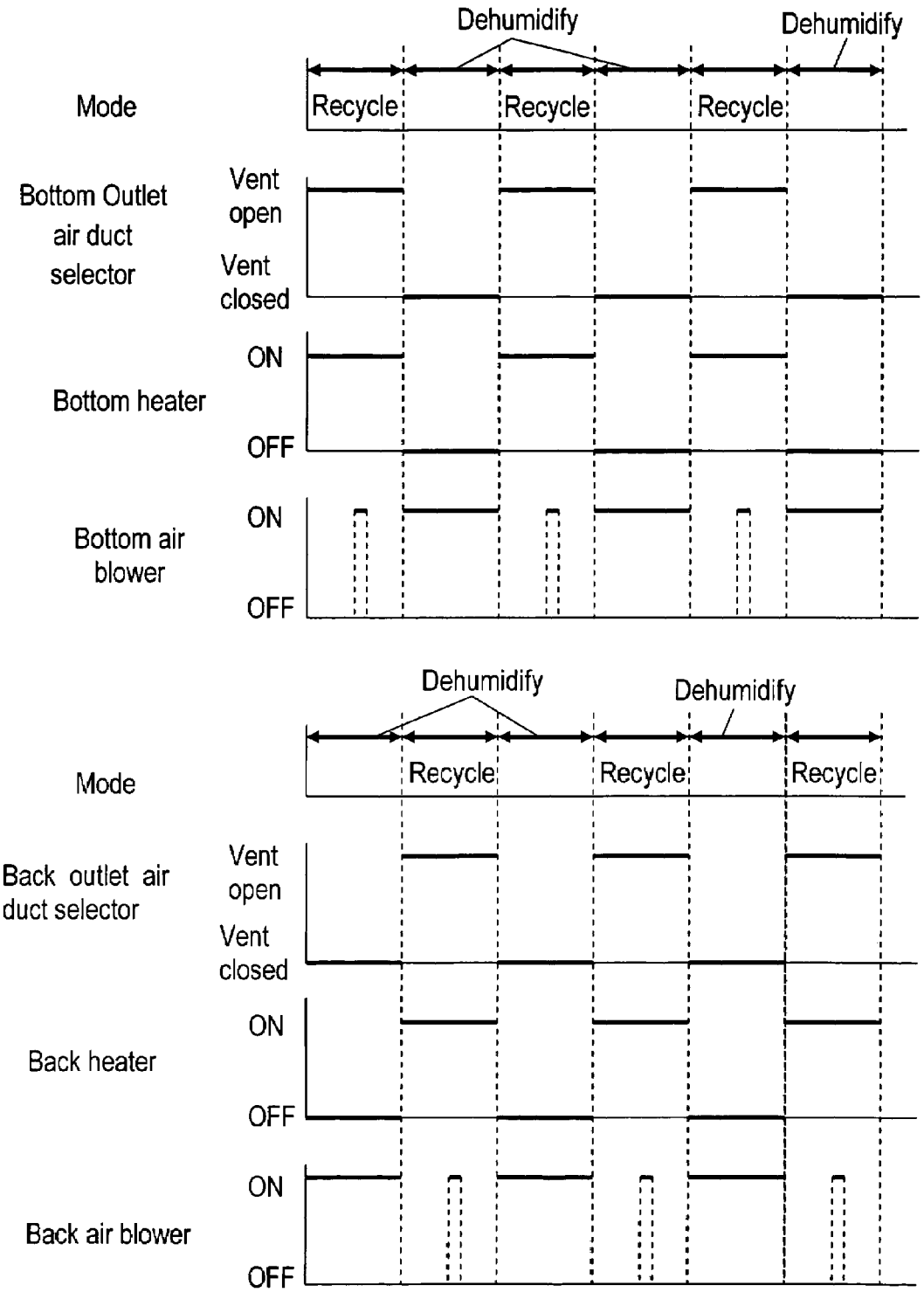
FIG. 13 shows time charts for the actions of dehumidifier in the bottom and back parts in each mode according to the seventh exemplary embodiment of the present invention.

FIG. 12 is a sectional block diagram of an air conditioning seat device according to a seventh exemplary embodiment of the present invention, and FIG. 13 shows time charts for the actions of dehumidifier in the bottom and back parts in each mode.

In FIG. 12, seat 54 has bottom part 71 and back part 72. Cooling air blowers (hereinafter, "blowers") 73A and 73B send in-cabin air to heat exchangers 64A and 64B for cooling the dehumidified air, respectively. In the figure, components with the same numbers as in the fourth embodiment through the sixth embodiment act in the same way. Particularly, a subscript A is attached to symbols for the air-conditioning unit and its parts of bottom part 71, and subscript B is attached to those of back part 72 for identification. In the above-mentioned makeup, when the operation is started as shown in FIG. 13, air-conditioning unit 52A in the bottom part performs the recycle mode operation. At this moment, outlet duct selector 66A opens a duct to vent 65A, heater unit 62A is activated, and air blower 51A stops for the first 20 seconds and then is activated for one second at a flow rate of 0.2 m$^3$/min. for example. From then on, these series of operations are performed in the recycle mode. In the case that the adsorbent of dehumidifier 51 is silica gel, vapor starts to desorb off the adsorbent when the adsorbent is heated to 120° C. Blower 50A emits the generated vapor from vent 65A to the inside of the cabin. Meanwhile, air-conditioning unit 52B of the back part performs the dehumidification mode operation first. In the dehumidification mode, outlet duct selector 66B closes the duct to vent 65B, and then blower 50B is activated. Blower 50B sends the in-cabin air at a flow rate of 0.2 m$^3$/min. for example. Dehumidifier 51B adsorbs the moisture of this air to decrease humidity. Owing to the adsorption heat at this moment, the air becomes 48° C. and 18% RH for example. The high-temperature and low-humidity air is introduced to heat exchanger 64B, indirectly cooled by in-cabin air from blower 73B, and becomes low-humidity air with 37° C. and 33% RH. Then the air is introduced to air duct 53B, blows out through holes 57B on skin 56, and flows on the side of human back to give coolness to the human body. At this moment, vaporization heat loss owing to vaporization of the sweat on the body surface gives coolness to a human body, suppressing steaminess.

Next as shown in FIG. 13, bottom part air-conditioning unit 52A performs the dehumidification mode operation, and back part air-conditioning unit 52B performs the recycle mode operation. Detail description for this operation is omitted because it is just one with the operations of bottom part air-conditioning unit 52A and back part air-conditioning unit 52B exchanged in the above-mentioned description.

If the above-mentioned operations are repeated from then on, when one air-conditioning unit is in the recycle mode, the other performs the dehumidification mode operation, and consequently the recycle mode operation is alternately performed. Such a makeup enables the dehumidified air to be continuously sent to a human body, enhancing coolness. In addition, even for a plurality of heater units, they do not operate simultaneously, and thus a maximum current for recycling requires that for one unit. Consequently, the load on an alternator for an automobile air conditioning seat device can be reduced, achieving a downsizing of an alternator. Also, independently providing bottom part air-conditioning unit 52A and back part air-conditioning unit 52B allows the setting level of humidity to be changed.

Although bottom part air-conditioning unit 52A and back part air-conditioning unit 52B are arranged at bottom part 71 and back part 72, respectively in FIG. 12, both of them may be arranged at either bottom part 71 or back part 72.

Exemplary Embodiment 8

Figure 14:
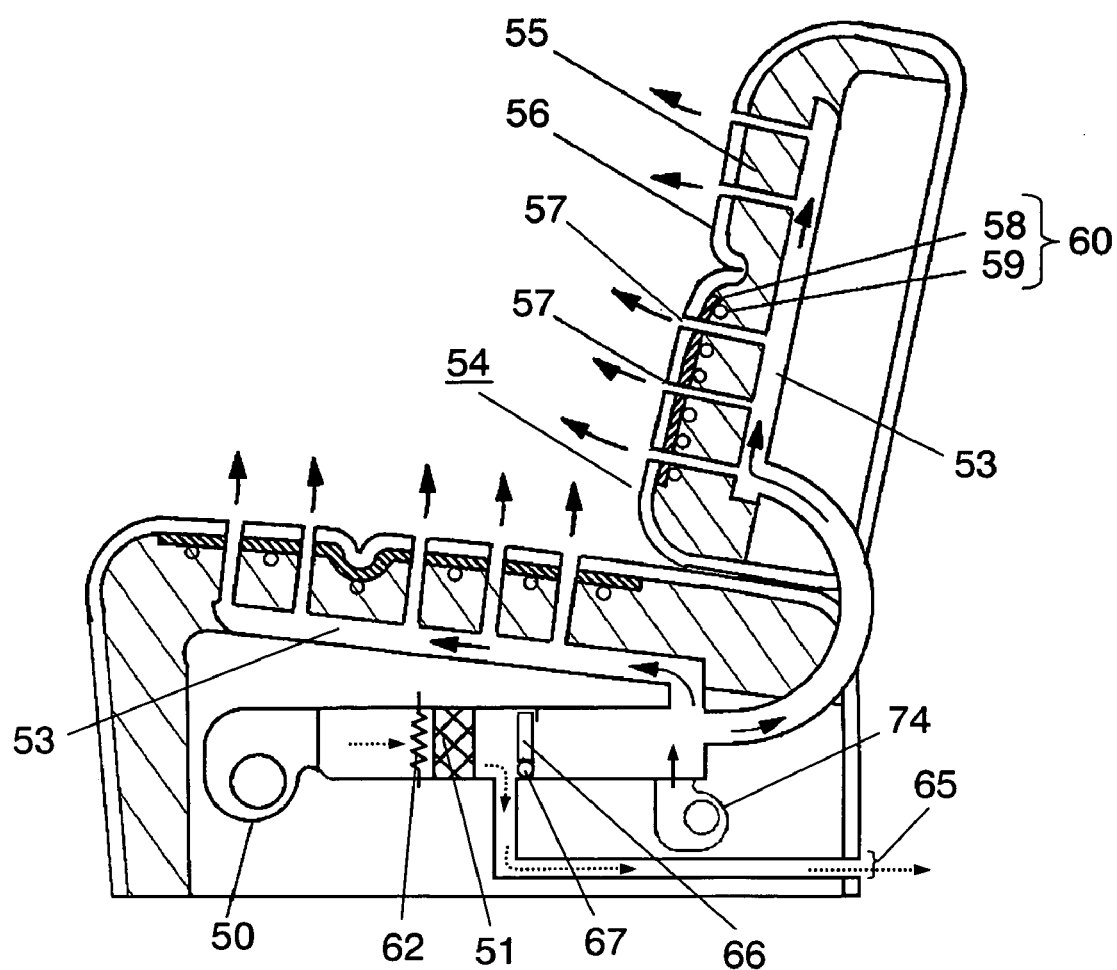
FIG. 14 is a sectional block diagram for illustrating the recycle mode in an air conditioning seat device according to an eighth exemplary embodiment of the present invention.

FIG. 14 is a sectional view of an air conditioning seat device in the recycle mode according to an eighth exemplary embodiment of the present invention. This embodiment differs from the fourth embodiment in that second air blower 74 is provided, and sends air to air duct 53 at least in the recycle mode. In the above-mentioned makeup, in the recycle mode, in which dehumidifier regains the dehumidification capability, stepping motor 67 is activated, and outlet duct selector 66 opens the duct to vent 65. Then, heater unit 62 is activated, and dehumidifier 51 regains its absorbability. At this moment, second air blower 74 is activated to introduce the in-cabin air to air duct 53 and blows it out through holes 57, giving coolness to a vehicle occupant. According to this makeup, coolness can be achieved even in the recycle mode. Further, switching the dehumidification mode and recycle mode repeatedly sends the dry air and the in-cabin air to a human body alternately. When the in-cabin air is sent, the clothes absorb moisture, and next, when the dry air is sent, vaporization latent heat loss of the clothes continuously gives a stronger coolness to a vehicle occupant, also in synergy with a fluctuation effect.

Exemplary Embodiment 9

Figure 15:
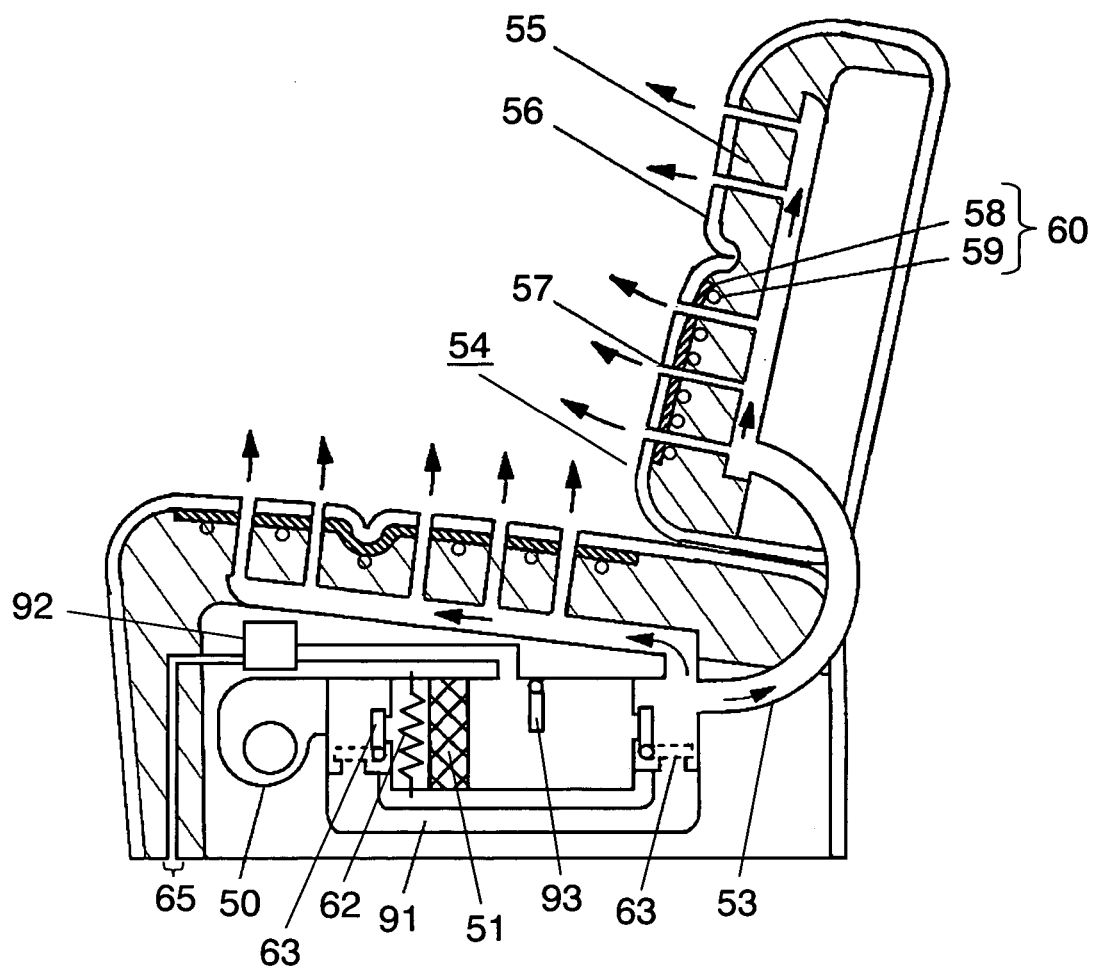
FIG. 15 is a sectional block diagram for illustrating the recycle mode in an air conditioning seat device according to a ninth exemplary embodiment of the present invention.

FIG. 15 is a sectional view of an air conditioning seat device in the recycle mode according to a ninth exemplary embodiment of the present invention. This embodiment differs from the second embodiment in that branch duct 91 is provided, which comes out from blower 50, branches in parallel with dehumidifier 51, and converges with air duct 53. Here, sealing part 63 switches the air sent from blower 50 to one of branch duct 91 and dehumidifier 51. In such a makeup, if the dehumidification capacity of dehumidifier 51 decreases during the dehumidification mode operation, sealing part 63 switches so that the air from blower 50 passes through branch duct 91, without flowing in dehumidifier 51. Then, the sent air blows out via air duct 53 through holes 57. These operations are also performed when dehumidifier 51 is not ready to dehumidify or only the operation for sending air is selected. For a sufficient dehumidification capacity of dehumidifier 51, sealing part 63 switches so that the air from blower 50 passes through dehumidifier 51. Accordingly, the sent air is, after dehumidified by dehumidifier 51, blows out via air duct 53 through holes 57. Consequently, sweat existing immediately after the operation started is dried with vaporization, which causes vaporization heat loss on the skin surface, suppresses steaminess due to the sweat by giving coolness, and when the dehumidified air is unnecessary, only the operation for sending air can be performed because the dehumidification capacity of dehumidifier 51 is decreased.

Further, in this embodiment, it is desirable to provide decompression unit 92 for removing the vapor generated by dehumidifier 51 in the recycle mode, and outlet duct selector 93. During the recycle mode operation, sealing part 63 seals dehumidifier 51 and heater unit 62. Then, heater unit 62 is activated to heat dehumidifier 51, and the adsorbed moisture is emitted. Next, selector 93 opens a duct to decompression unit 92, which is then activated. This desorbs the moisture adsorbed by the adsorbent in dehumidifier 51, to regain the dehumidification capacity of dehumidifier 51. In this case, dehumidifier 51 is cooled owing to desorption heat loss. In such a makeup, the air sent by blower 50 is dehumidified and also cooled by low-temperature dehumidifier 51, in the dehumidification mode, the low-temperature and low-humidity air is introduced to air duct 53 and blows out through holes 57, giving a strong coolness to a vehicle occupant owing to the send air. In addition, blower 50 is activated to introduce the in-cabin air to air duct 53, and then the air blows out through holes 57 in the recycle mode, giving coolness to a vehicle occupant owing to the send air. Therefore, this makeup provides coolness even in the recycle mode.

In this embodiment, decompression unit 92 decompresses the air to remove vapor after heater unit 62 heats dehumidifier 51. However, heater unit 62 is not necessarily required depending on the switching frequency between the dehumidification mode and recycle mode, and the operation environment. In such a case, the following method may be also used, namely, instead of removing the moisture desorbing off heater unit 51 by decompression unit 92, after desorbing vapor by decompression, while the seat is unoccupied, blower 50 blows out the air via air duct 53 through holes 57.

Exemplary Embodiment 10

Figure 16:
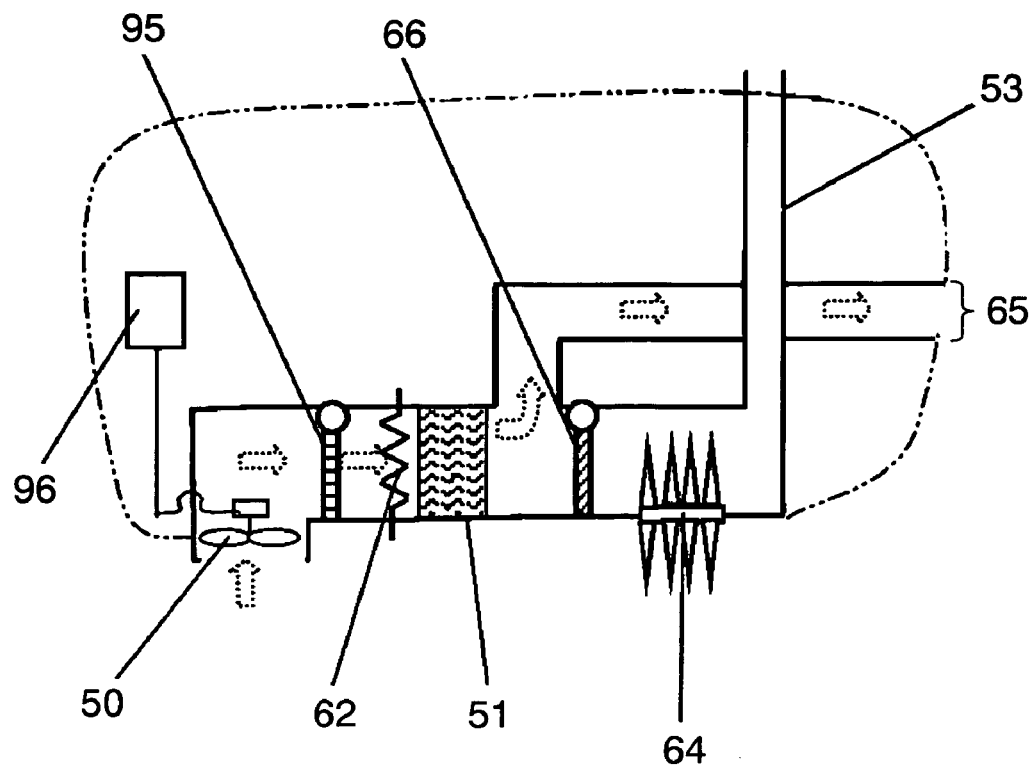
FIG. 16 is a sectional block diagram of the air-conditioning unit in an air conditioning seat device according to a tenth exemplary embodiment of the present invention.

FIG. 16 is a block diagram of an air-conditioning unit according to a tenth exemplary embodiment of the present invention and shows how it operates in the recycle mode. This embodiment differs from bottom part air-conditioning unit 52A in the seventh embodiment in that air-volume adjuster (hereinafter, "adjuster") 95 is provided for adjusting a blow volume from blower 50. In the recycle mode, the opening of adjuster 95 is adjusted so that the air to be sent to dehumidifier 51 becomes a feeble wind with a blow volume of approximately 0.02 m³/min. for example. Namely, it is approximately ⅒ of air-volume in the dehumidification mode. By doing so, the temperature rise of dehumidifier 51 by heater unit 62 is accelerated, and at the same time, the vapor desorbed off dehumidifier 51 is removed by the send air. Accordingly, the adsorbent in dehumidifier 51 can be recycled quickly. In other words, the operating time in the dehumidification mode becomes relatively long and coolness is intensified.

In the recycle mode, heater unit 62 is desirably made of a heater generating radiant energy in order to efficiently heat dehumidifier 51 for heater unit 62. Such kinds of heaters typically include a halogen heater, and a pipe heater having a heating element in the ceramic pipe, both generating radiant energy. In addition, the direction of energy radiation is set to that of the duct for dehumidifier 51. Such heater unit 62 is arranged in the duct, and thus, if it is tubelike, the resistance against the send air becomes small. Such a makeup may be applied to the other embodiments. Further, it is desirable that adjuster 95 and selector 66 are made of a mirror-surface material, and to make the radiant energy from heater unit 62 reflect to a direction of dehumidifier 51. As a mirror-surface material, a stainless-steel mirror surface material for example is used with a radiation rate of approximately 0.1 to 0.3.

Alternatively, making the adsorbent in dehumidifier 51 contact heater unit 62 made of electrical resistance heating wire for example, also cause dehumidifier 51 to be heated efficiently in the recycle mode.

The air-conditioning unit in FIG. 16 has controller 96 for adjusting the blow capacity of blower 50. The same effect as mentioned above can be achieved also by having the air blower blow feeble wind using controller 96. Using a motor with variable revolution such as a DC motor for blower 50 implements such a control easily. Although the air-conditioning unit in FIG. 16 has both adjuster 95 and controller 96, a method also works where the air-conditioning unit has either of them and the blow volume in the recycle mode is adjusted.

In FIG. 16, the duct to vent 65 is arranged at a position higher than dehumidifier 51. The air including the vapor generated in the recycle mode is in a high temperature, and thus in such a makeup, the discharged air becomes a rising air current, generating a current in which air from the cabin flows into the adsorbent. Alternatively, even the send air by blower 50 is feeble as mentioned above, the air including vapor is easily discharged owing to this rising air current, shortening the recycle time of dehumidifier 51.

Exemplary Embodiment 11

Figure 17:
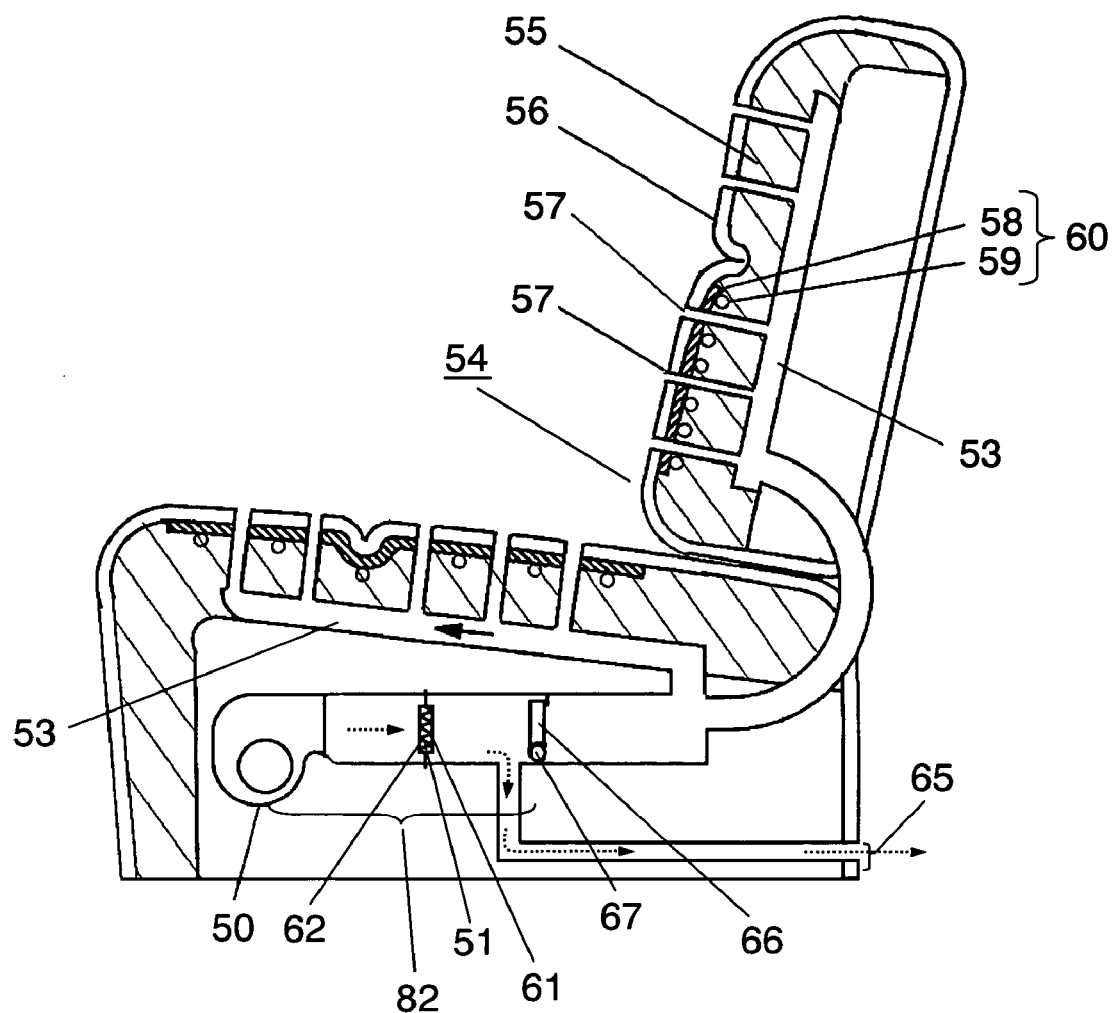
FIG. 17 is a sectional block diagram for illustrating the recycle mode in an air conditioning seat device according to an eleventh exemplary embodiment of the present invention.
Figure 18:
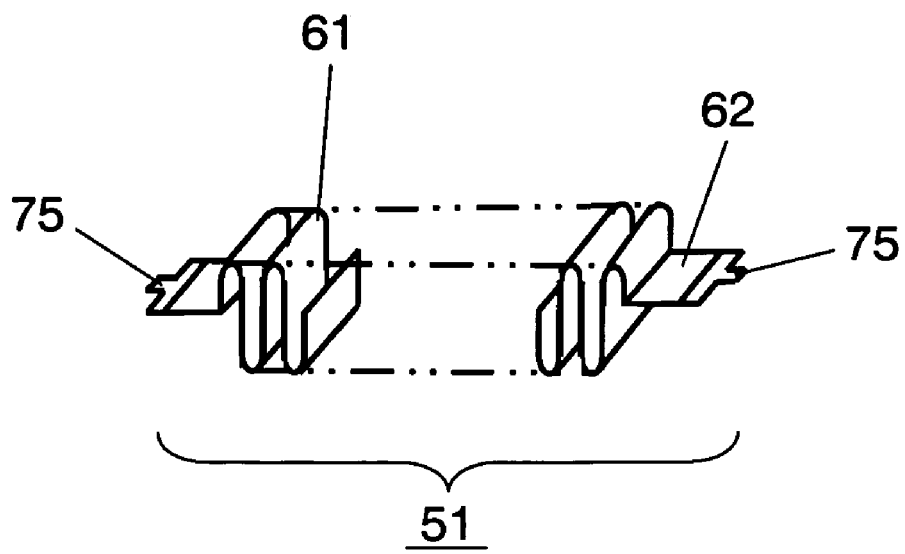
FIG. 18 is a perspective view of a dehumidifier according to the eleventh exemplary embodiment of the present invention.
Figure 19:
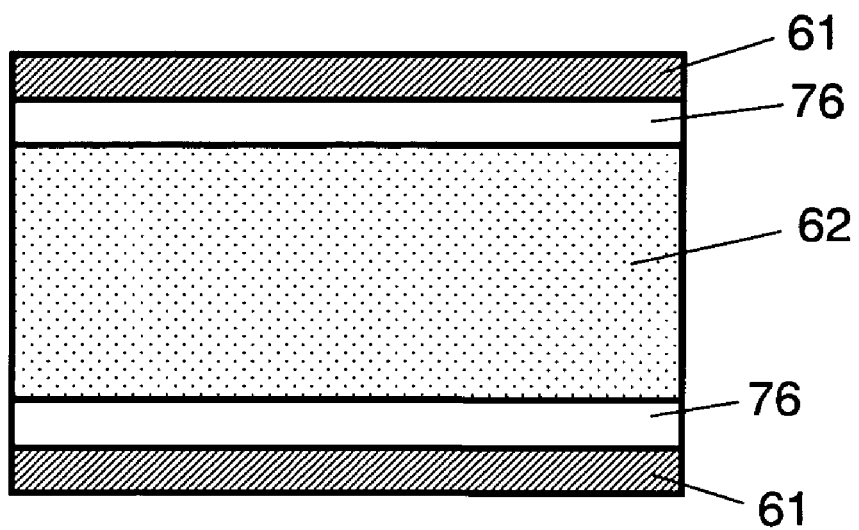
FIG. 19 is a sectional view of the dehumidifier according to the eleventh exemplary embodiment of the present invention.

FIG. 17 is a sectional view of an air conditioning seat device in the recycle mode according to an eleventh exemplary embodiment of the present invention, FIG. 18 is a perspective view of a dehumidifier, and FIG. 19 is a sectional view of the dehumidifier. This embodiment differs from the fourth embodiment in a makeup where the surface of heater unit 62 supports an adsorbent as dehumidifier 51. Heater unit 62, made of a strip-shaped, pleating-processed electrical resistance heating element as shown in FIG. 18, removes moisture in adsorbent 61, energized from terminal 75.

In FIG. 19, dehumidifier 51 has a makeup where the surface of heater unit 62 has undercoat layer 76, and also supports adsorbent 61 thereon. Undercoat layer 76, made of oxide sintered and oxidized of such as aluminum hydroxide, or cerium nitrate, chemically bonds with adsorbent 61, improving adhesion. Meanwhile, if undercoat layer 76 has a makeup where glass frit is coated and sintered, the surface of undercoat layer 76 becomes bumpy. Accordingly, in addition to the above-mentioned chemical bond, a physical anchor effect further improves adhesion. With such undercoat layer 76, repeated heating and cooling does not cause adsorbent 61 to exfoliate, and thus increasing the durability.

In this embodiment, dehumidifier 51 includes heater unit 62 therein, and thus the heat from heater unit 62 directly transfers to absorbent material 61 in the recycle mode, increasing the temperature-rise speed of the adsorbent. In other words, even for a short recycle time, most of the adsorbed vapor is discharged. Consequently, air-conditioning unit 82 according to this embodiment regains its absorbability in a short time, and thus even if the dehumidification mode and recycle mode are repeated intermittently, sufficient dehumidification capacity is delivered. Accordingly, a drastic downsizing of dehumidifier 51 is achieved, facilitating installation of dehumidifier 51 in the main body of a seat. Further, adsorbent 61 is directly heated, which means air itself is less heated and the power consumption is small in the recycle mode. Still, even after a long time with no use, the absorbability of dehumidifier 51 can be recycled in a short time, dispensing with a strict sealing structure for preventing adsorption of vapor in the atmospheric air, and achieving a downsizing of an air-conditioning unit.

Heater unit 62 is pleating-processed in a form of a corrugated plate, increasing the area where adsorbent 61 contacts air, decreasing the space occupied by adsorbent 61, and downsizing air-conditioning unit 82 as a whole.

Figure 20:
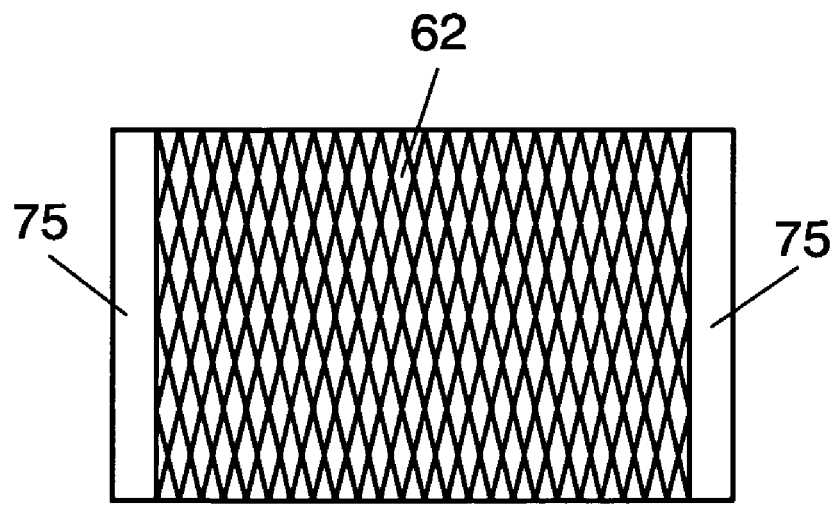
FIG. 20 is a developed view of the dehumidifier according to the eleventh exemplary embodiment of the present invention.
Figure 21:
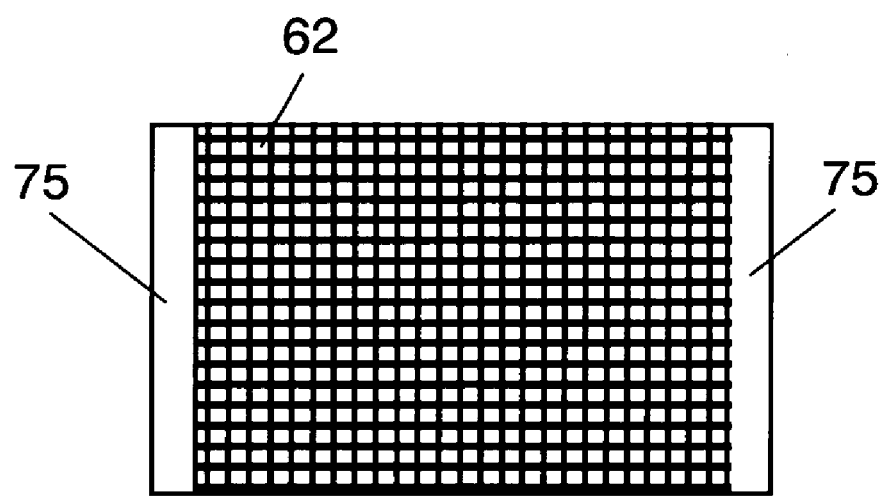
FIG. 21 is a developed view of another dehumidifier according to the eleventh exemplary embodiment of the present invention.
Figure 24:
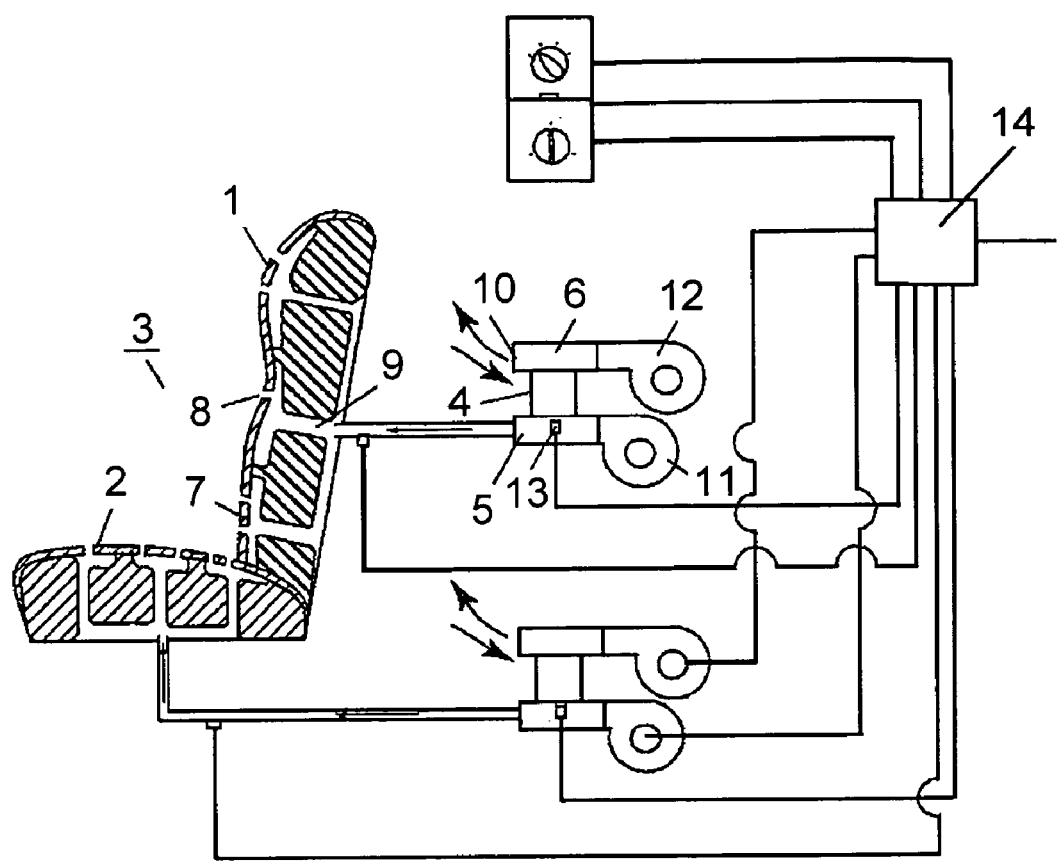
FIG. 24 is a block diagram of an air conditioning seat device in the first conventional example.
Figure 25:
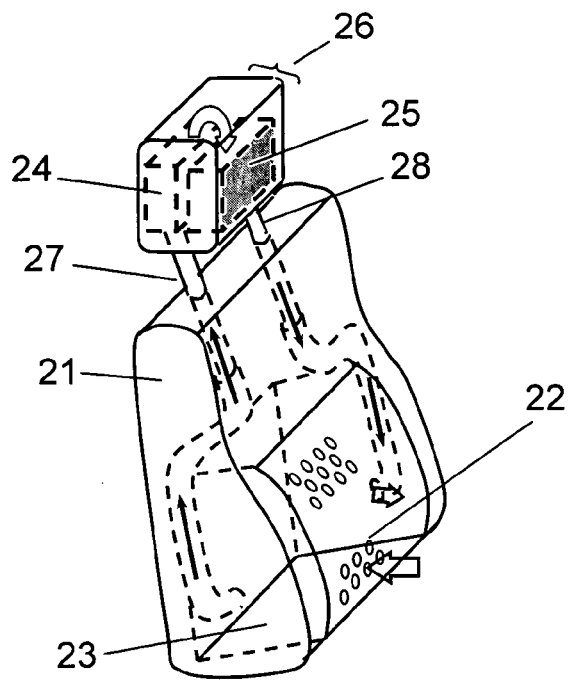
FIG. 25 is perspective view of an air conditioning seat device in the second conventional example.
Figure 26:
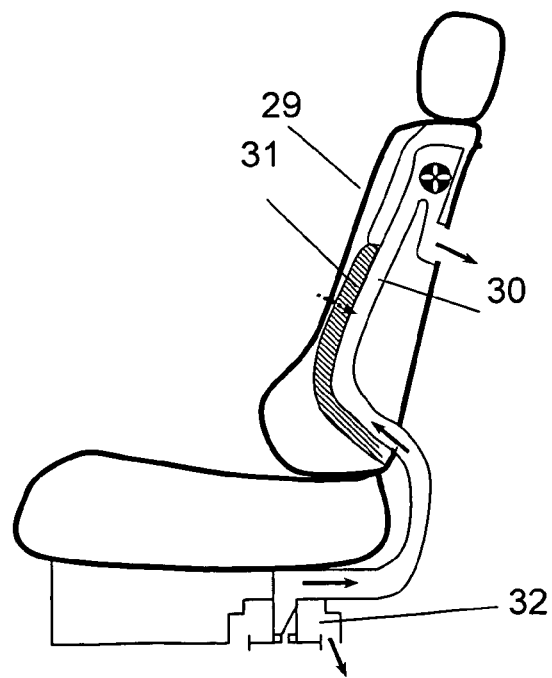
FIG. 26 is a sectional view of an air conditioning seat device in the third conventional example.
Figure 27:
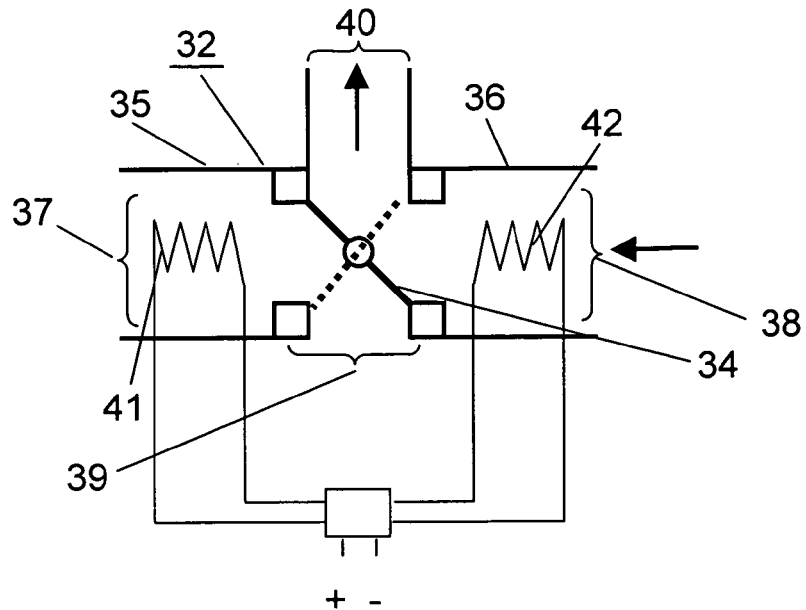
FIG. 27 is a sectional view of an air dryer unit in FIG. 26.
Figure 28:
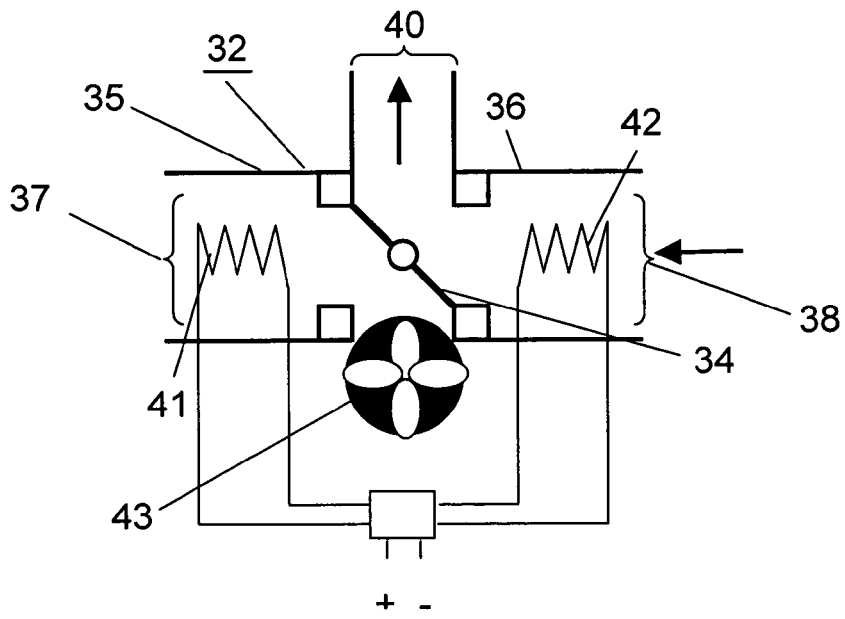
FIG. 28 is a sectional view of another air dryer unit in FIG. 26.

FIGS. 20 through 22 are schematic diagrams of heater unit 62 with terminals 75 at both ends. In FIG. 20, heater unit 62 is made of an expand-metal which is a lacinia-processed and expanded metal thin plate such as stainless-steel. In FIG. 21, heater unit 62 is made of a wire mesh which is a netted stainless-steel metal wire. In FIG. 22, heater unit 62 is made of a porous member such as a punched stainless-steel thin plate. In the above-mentioned makeup, specifications of notch for lacinia of an expand-metal, elemental wire thickness and interval of weave pattern of a wire mesh, or punching specifications for hole diameter and pitch of punching metal can be easily changed. These changes allow the resistance value of the metallic body to be adjusted with ease and high accuracy, and thus a desired heating element can be easily obtained. In addition, heater unit 62, a porous member, can easily support adsorbent 61 by dipping, for example. Still, the mesh of heater unit 62, made of such as an expand-metal, is open, and thus air widely contacts adsorbent 61 in the dehumidification mode. Accordingly, the adsorption speed per unit volume of dehumidifier 51 is increased, downsizing air-conditioning unit 82. Further, such a heater unit 62, a porous member, reduces the pressure loss of the send air. In the recycle mode, heater unit 62 is heated with power applied to terminal 75, which is welded so that terminal 75 contacts the whole end surface of such as an expand-metal. An expand-metal, a wire mesh, or a punched plate is a thin plate with lacinia or thin wire, has a low heat-capacity with a same electrical resistance as compared with a regular thin plate, decreasing the recycle time.

If heater unit 62 is covered therearound with an electric insulator, a metal can be used for the dehumidification duct with dehumidifier 51 arranged therein without an electric leak. This results in protecting heater unit 62, preventing adsorbent 61 on the surface from being damaged in conveying and assembling.

If heater unit 62 is surrounded by a heat insulating material, the heat caused by heater unit 62 is prevented from transferring to somewhere other than dehumidifier 51, to the ambient air for example, allowing dehumidifier 51 to be efficiently heated.

If a large number of projections are provided on the surface of heater unit 62, the airflow near adsorbent 61 becomes a turbulent flow, facilitating a contact of the airflow and adsorbent 61. This encourages dehumidifier 51 to adsorb moisture, improving absorbability, and to reduce the recycle time.

As an example, dehumidifier 51 is made of a carrier corrugate-processed with ceramic paper filtering ceramic fiber and silica gel as an adsorbent supported thereon, and heater unit 62 is made of a nichrome wire. In such a makeup, it takes approximately five minutes to desorb moisture of 1 g when a power of 100 W is applied to heater unit 62 in the recycle mode. On the other hand, in this embodiment, it takes only approximately 30 seconds to desorb moisture of 1 g under the same conditions, a power of 100 W, in the recycle mode. Therefore, even if recycling is started at the same time seating started, the dehumidification mode operation starts in 30 seconds, giving coolness to a vehicle occupant immediately after seating in summer. FIG. 23 shows the measured temperatures of a back surface of a male in his 20's, and the declared values of coolness on his back in the repeated operations of: recycle mode 30 seconds—dehumidification mode 30 seconds—recycle mode 30 seconds—dehumidification mode 30 seconds. The measurement conditions are as following: in the cabin; ambient temperature 35° C., humidity 55% RH, blowout air; 0.2 m³/min., temperature 37° C., humidity 20% RH, no send air during the recycle mode operation. As shown in the figure, the body temperature rises due to heat from the seat for the first 30 seconds, which is in recycling, however, after 30 seconds to one minute, the body temperature falls by approximately 3° C. Then, the declared value of coolness reaches the level "a little cool," which means the vehicle occupant feels a strong coolness. From then on, the body temperature slightly rises in the recycle mode, and slightly falls in the dehumidification mode. As this situation repeats, the body temperature gradually rises to return to the steady state. However, the declared value of coolness sustains "a little cool," because of feeling a strong coolness owing to fluctuation effect, and reduction of moisture on the back. In addition, as long as the intermittent interval is 30 seconds or shorter, a vehicle occupant does not feel uneasy about a sense of warmth while the dehumidification air is not blown out.

In a case where the temperature of skin 56 is high due to insolation for example, the blow out air is heated by the heat of skin 56 when an air-conditioning unit starts its operation in which low-temperature, high-humidity air is blown out. Therefore, it takes some time until coolness is given to a vehicle occupant. Meanwhile, in the embodiment of the present invention, coolness can be quickly given to vehicle occupant because dry air is directly applied. Still, the capacity to remove moisture is high. Although the description is made assuming that the blow volume of blower 50 is 0.2 m³/min., the present invention is not limited to this condition.

Although the above-mentioned embodiment is described for a case where the apparatus is mounted on a vehicle, the present invention may be applied to a seat in an office, for example.

Hereinbefore, embodiments of the present invention are described, where a makeup specific to each embodiment can be embodied in combination with another embodiment, and such a combination is included in the present invention.

INDUSTRIAL APPLICABILITY

According to the present invention, the air sent by a dehumidifying air blower is dehumidified by a dehumidifier, and then the dehumidified air blows out through the blow-out holes on the seat skin. In this makeup, although a human body is heated with heat transmission from the dehumidified air and contact heat transmission from the seat skin, the sweat on the body surface and in the clothes is rapidly vaporized, causing a large amount of vaporization heat loss. Accordingly, the human body feels coolness, and steaminess on the skin is suppressed owing to the sweat vaporization. Further, the present invention does not need to process dew condensation water, generates dry air quickly, and allows continuous operation. In such a way, a comfortable air conditioning seat device is provided.

| Reference marks in the drawings | |
|---|---|
| 1 | Backrest |
| 2 | Seating part |
| 3 | Seat |
| 4 | Peltier module |
| 5 | Main heat exchanger |

| -continued | |
|---|---|
| Reference marks in the drawings | |
| 6 | Waste-heat heat exchanger |
| 7 | Surface cover |
| 8 | Airflow blow-out hole |
| 9 | Air duct |
| 10 | Waste-heat air duct |
| 11 | Main fan |
| 12 | Auxiliary fan |
| 13 | Temperature sensor |
| 14 | Controller |
| 21 | Main body of seat |
| 22 | Skin cloth |
| 23 | Air bag |
| 24 | Cooler/dehumidifier |
| 25 | Heater/dryer |
| 26 | Dehumidifier/dryer |
| 27 | Inlet air duct |
| 28 | Outlet air duct |
| 29 | Backrest |
| 30 | Air duct |
| 31 | Moisture-permeable layer |
| 32 | Air dryer |
| 34 | Air flap |
| 35, 36 | Reaction box |
| 37, 38 | Air inlet |
| 39, 40 | Air outlet |
| 41, 42 | Electric heater |
| 43 | Fan |
| 50, 50A, 50B | Dehumidifying blower |
| 51, 51A, 51B | Dehumidifier |
| 52, 52A, 52B, 82 | Air-conditioning unit |
| 53, 53A, 53B | Air duct |
| 54 | Seat |
| 55 | Pad |
| 56 | Skin |
| 57, 57A, 57B | Blow-out hole |
| 58 | Seat |
| 59 | Heater wire |
| 60 | Heater |
| 61 | Absorbent material |
| 62, 62A, 62B | Heater unit |
| 63 | Sealing part |
| 64, 64A, 64B | Heat exchanger |
| 65, 65A, 65B | Vent |
| 66, 66A, 66B, 93 | Outlet air duct selector |
| 67 | Stepping motor |
| 68 | Outlet air duct |
| 70 | Temperature detector |
| 71 | Bottom |
| 72 | Back |
| 73A, 73B | Cooling air blower |
| 74 | Air blower |
| 75 | Terminal |
| 76 | Undercoat layer |
| 77 | Humidity detector |
| 91 | Branch duct |
| 92 | Decompression unit |
| 95 | Air volume adjuster |
| 96 | Controller |

The invention claimed is:

1. An air-conditioning seat apparatus comprising:
a main body of a seat, the main body having a surface at least a portion of which contacts a person seated in the seat, the surface facing the person seated in the seat, a plurality of holes being formed in the surface;
a first air blower that takes in air from an area other than the surface of the main body of the seat;
a dehumidifier for dehumidifying air sent by the first air blower, the dehumidifier including an absorbent generating heat when absorbing moisture;
an air duct for sending air dehumidified by the dehumidifier, from the dehumidifier to the holes formed in the main body of the seat, and at least one sealing part positioned between the first air blower and the dehumidifier for preventing moisture in the air from reaching the dehumidifier while the dehumidifier is not operational, wherein air dehumidified by the dehumidifier blows out through the holes formed in the surface of the main body of the seat.

2. The air conditioning seat device according to claim , further comprising:

a heater unit for heating the dehumidifier.

3. The air conditioning seat device according to claim 2, further comprising:

a vent communicating from the dehumidifier to an outside of the main body of the seat; and a selector for opening and closing the vent.

4. The air conditioning seat device according to claim 2, further comprising a controller;

wherein the controller activates the heater unit, and makes the blow volume of the first air blower reduced in a recycle mode, in which the dehumidification capability of the dehumidifier is regained; and the controller stops the heater unit, and operates the first air blower in a dehumidification mode, in which the air dehumidified by the dehumidifier is blown out through the holes.

5. The air conditioning seat device according to claim 4, wherein the dehumidifier is one of dehumidifiers, at least one of the dehumidifiers performs an operation of the dehumidification mode; and at the same time, at least one of the other dehumidifiers performs an operation of the recycle mode.

6. The air conditioning seat device according to claim 2 further comprising a controller;

wherein the controller stops the heater unit and operates the first air blower until the absorbent cools to a set temperature in a recycle mode, in which the dehumidification capability of the dehumidifier is regained, by when entering a dehumidification mode, in which the air dehumidified by the dehumidifier is blown out through the holes.

7. The air conditioning seat device according to claim 6, wherein the dehumidifier is one of dehumidifiers, at least one of the dehumidifiers performs an operation of the dehumidification mode; and at the same time, at least another of the dehumidifiers performs an operation of the recycle mode.

8. The air conditioning seat device according to claim 2, further comprising:

a second air blower for sending air to the air duct.

9. The air conditioning seat device as claimed in claim 8, further comprising a controller;

wherein the controller operates the second air blower at least in a recycle mode, in which the dehumidification capability of the dehumidifier is regained.

10. The air conditioning seat device according to claim 2, wherein the heater unit includes one of:

an expand-metal that is a lacinia-processed and expanded metal thin plate;

a wire mesh which is a netted metal wire; and a porous member that is a hole-punched metal thin plate, and generates heat by applying a current to one of the expand-metal, the wire mesh, and the porous member.

11. The air conditioning seat device according to claim 1, wherein the air duct is made of an unabsorbent material.

12. The air conditioning seat device according to claim 1, wherein the main body of the seat has a pad therein and a skin for covering the pad, a moisture-absorbing member is further provided between the pad and the skin, and air from the air duct passes through the moisture-absorbing member and then blows out through the holes.

13. The air conditioning seat device according to claim 1, wherein the main body of the seat has a pad therein and a skin for covering the pad, a heater is further provided between the pad and the skin.

14. The air conditioning seat device according to claim 1, further comprising:

a sealing part for sealing the dehumidifier; and a decompression unit for decompressing and drying the dehumidifier.

15. The air conditioning seat device according to claim 1, wherein the dehumidifying mode and a recycle mode repeat and the respective time periods for each mode increase as the modes repeat.

16. The air conditioning seat device according to claim 1, further comprising:

a heat exchanger for cooling the air dehumidified and heated by the dehumidifier, the heat exchanger being provided in the air duct between the dehumidifier and the holes.

17. An air conditioning seat device, comprising:

a main body of a seat, the main body having a surface at least a portion of which contacts a person seated in the seat, the surface facing the person seated in the seat, a plurality of holes being formed in the surface;

a first air blower that takes in air from an area other than the surface of the main body of the seat;

a dehumidifier for dehumidifying air sent by the first air blower, the dehumidifier including an absorbent generating heat when absorbing moisture;

an air duct for sending air dehumidified by the dehumidifier, from the dehumidifier to the holes formed in the main body of the seat, and a heater unit for heating the dehumidifier, wherein the adsorbent included in the dehumidifier is fixed on the heater.

18. An air-conditioning seat apparatus comprising:

a main body of a seat, the main body having a surface at least a portion of which contacts a person seated in the seat, the surface facing the person seated in the seat, a first hole being formed in the surface;

a first air blower that takes in air from an area other than the surface of the main body of the seat;

a dehumidifier for dehumidifying air sent by the first air blower, owing to adsorption;

an air duct for sending air dehumidified by the dehumidifier, from the dehumidifier to the first hole formed in the main body of the seat, a heater unit for heating the dehumidifier;

a controller for controlling the air-conditioning seat apparatus to switch between (a) a dehumidifying mode and (b) a recycle mode; and at least one sealing part positioned between the first air blower and the dehumidifier;

wherein, during the dehumidifying mode, air dehumidified by the dehumidifier blows out through the first hole formed in the surface of the main body of the seat; and during the recycle mode, moist air is blown out of a second hole formed in the main body of the seat, the heater is on and the first air blower is turned on and off intermittently and the at least one sealing part is closed to prevent moisture in the air from reaching the dehumidifier.

\* \* \* \* \*

UNITED STATES PATENT AND TRADEMARK OFFICE
CERTIFICATE OF CORRECTION

PATENT NO. : 7,581,584 B2
APPLICATION NO. : 10/507759
DATED : September 1, 2009
INVENTOR(S) : Noriyuki Yoneno et al.

It is certified that error appears in the above-identified patent and that said Letters Patent is hereby corrected as shown below:

At Column 17, line 8, "according to claim ," should read -- according to claim 1, --

Signed and Sealed this

Nineteenth Day of January, 2010

David J. Kappos
*Director of the United States Patent and Trademark Office*